US008062842B2

(12) United States Patent
Vanmechelen et al.

(10) Patent No.: US 8,062,842 B2
(45) Date of Patent: Nov. 22, 2011

(54) METHOD FOR DETERMINING THE RISK OF DEVELOPING A NEUROLOGICAL DISEASE

(75) Inventors: Eugeen Vanmechelen, Nazareth-Eke (BE); Lieve Nuytinck, Drongen (BE)

(73) Assignee: Abbott Healthcare Products B.V., Weesp (NL)

( * ) Notice: Subject to any disclaimer, the term of this patent is extended or adjusted under 35 U.S.C. 154(b) by 110 days.

(21) Appl. No.: 12/157,494

(22) Filed: Jun. 10, 2008

(65) Prior Publication Data

US 2008/0261889 A1   Oct. 23, 2008

Related U.S. Application Data

(63) Continuation of application No. 11/063,716, filed on Feb. 23, 2005, now abandoned.

(60) Provisional application No. 60/552,847, filed on Mar. 12, 2004.

(30) Foreign Application Priority Data

Feb. 24, 2004  (EP) .................................... 04447050
Jun. 29, 2004  (EP) .................................... 04103052

(51) Int. Cl.
  *C12Q 1/68*   (2006.01)
  *C07H 21/04*  (2006.01)
  *C12P 19/34*  (2006.01)

(52) U.S. Cl. ........................... 435/6; 536/24.3; 435/91.2

(58) Field of Classification Search ........................ None
See application file for complete search history.

(56) References Cited

U.S. PATENT DOCUMENTS

| | | | |
|---|---|---|---|
| 4,391,904 A | 7/1983 | Litman et al. | |
| 5,208,036 A | 5/1993 | Eppstein et al. | |
| 5,264,618 A | 11/1993 | Felgner et al. | |
| 5,283,185 A | 2/1994 | Epand et al. | |
| 5,399,346 A | 3/1995 | Anderson et al. | |
| 6,562,784 B1 | 5/2003 | Thiel et al. .................. | 514/8 |
| 2003/0092019 A1 | 5/2003 | Meyer et al. ..................... | 435/6 |

FOREIGN PATENT DOCUMENTS

| | | |
|---|---|---|
| JP | A-2000-143699 | 5/2000 |
| JP | 2007528219 | 10/2007 |
| WO | WO 95/05853 | 3/1995 |
| WO | WO 96/29605 | 9/1996 |
| WO | WO 01/04349 | 1/2001 |
| WO | WO 02/05833 | 1/2002 |
| WO | WO 03/090774 | 11/2003 |
| WO | WO 2005/080594 | 9/2005 |

OTHER PUBLICATIONS

Benner et al (Trends in Genetics (2001) vol. 17, pp. 414-418).*
Kelly et al., "*Rapid and Sensitive Method for Detection of Y402, H402,I62, and V62 Variants of Complement Factor H in Human Plasma Samples Using Mass Spectrometry*," Invest Ophthalmol Vis Sci., Apr. 2009; vol. 50, No. 4, pp. 1540-1545.

Hirokawa et al., "*Anti-TSI-RNA: Characterization of Novel Antibodies Against Sequence-Specific RNA by Random RNA Selection in Patients with Sjogren's Syndrome*," J. Rheumatol, 2002, vol. 29, pp. 931-937.
Meyer et al., "*MALDI-TOF MS Genotyping of Polymorphisms Related to 1-Carbon Metabolism Using Common and Mass-Modified Terminators*," Clinical Chemistry, 2009, vol. 55, No. 1, pp. 139-149.
Lanzrein A-S et al. (1998), Mannan-binding lectin in human serum, cerebrospinal fluid and brain tissue and its role in Alzheimer's disease, *NeuroReport* 9:1491-1495.
Hans O et al. (1995), Interplay between promoter and structural gene variants control basal serum level of mannan-binding protein, *The Journal of Immunology* 155:3013-3020.
Emahazion T et al. (2001), SNP association studies in Alzheimer's disease highlight problems for complex disease analysis, *Trends in Genetics* 17:407-413.
Scott WK et al. (2003), Ordered-subsets linkage analysis detects novel Alzheimer disease loci on chromosomes 2q34 and 15q22, *Journal of Human Genetics* 73:1041-1051.
Hibberd ML et al. (1999), Association of variants of the gene for mannose-binding lectin with susceptibility to meningococcal disease, *The Lancet* 252:1049-1053.
Tang M-X et al. (1998), The $APOE$-$\epsilon 4$ allele and the risk of Alzheimer disease among African Americans, whites, and Hispanics, *JAMA* 279:751-755.
Bernig T et al. (2004), Sequence analysis of the mannose-binding lectin ($MBL2$) gene reveals a high degree of heterozygosity with evidence of selection, *Genes and Immunity* 5:461-476.
Tang Y-W et al. (2000), Analysis of candidate-host immunogenetic determinants in herpes simplex virus-associated Mollaret's meningitis, *Clinical Infectious Diseases* 30:176-178.
Alafuzoff I., Iqbal K., Friden H., Adolfsson R., Winblad B. (1987) Histopathological criteria for progressive dementia disorders: clinical-pathological correlation and classification by multivariate data analysis. Acta Neuropathol. (Berl) 74: 209-225.
Alloul K., Sauriol L., Kennedy W., Laurier C., Tessier G., Novosel S. et al. (1998) Alzheimer's disease: a review of the disease, its epidemiology and economic impact. Arch. Gerontol. Geriatr. 27: 189-221.
Armstrong M., Daly A.K., Cholerton S., Bateman D.N., Idle J.R. (1992) Mutant debrisoquine hydroxylation genes in Parkinson's disease. Lancet 339: 1017-1017.
Artiga M.J., Bullido M.J., Sastre., Recuero M., Garcia M.A., Aldudo J., Vazquez J., Valdivieso F. (1998) Allelic polymorphisms in the transcriptional regulatory region of apolipoprotein E gene. FEBS Lett. 421: 105-108.
Benner et al., Evolution, language and analogy in functional genomics, Trends in Genet., vol. 17 (2001), pp. 414-418.
Boldt A.B., Petz-Erler M.L. (2002) A new strategy for mannose-binding lectin gene haplotyping. Hum. Mutat. 19: 296-306.
Brayden D.J., Templeton L., McClean S., Barbour R., Huang J., Nguyen M., Ahem D., Motter R., Johnson-Wood K., Vasquez N., Schenk D., Seubert P. (2001) Encapsulation in biodegradable microparticles enhances serum antibody response to parenterally-delivered βamyloid in mice. Vaccine 19: 4185-4193.
Campion D., Dumanchin C., Hannequin D., Dubois B., Belliard S., Puel M., Thomas-Anterion C., Michon A., Martin C., Charbonnier F., Raux G., Camuzat A., Penet C., Mesnage V., Martinez M., Clerget-Darpoux F., Brice A., Frebourg T. (1999) Earlyonset autosomal dominant Alzheimer disease: prevalence, genetic heterogeneity, and mutation spectrum. Am. J. Hum. Genet. 65: 664-670.

(Continued)

*Primary Examiner* — Steven Pohnert
(74) *Attorney, Agent, or Firm* — Finnegan, Henderson, Farabow, Garrett & Dunner, L.L.P.

(57) ABSTRACT

Methods and kits are provided for determining whether a subject is at risk of developing a neurological disease such as Alzheimer's disease and multiple sclerosis. The methods and kits are based on the detection of one or more nucleic acid variants in the MBL gene of the subject.

6 Claims, 1 Drawing Sheet

OTHER PUBLICATIONS

Celis J.E., Gromov P., Ostergaard M., Madsen P., Honore B., Dejgaard K., Olsen E., Vorum H., Kristensen D.B., Gromova I., Haunso A., Van Damme J., Puype M., Vandekerckhove J., Rasmussen H.H. (1996). Human 2-D Page databases for proteome analysis in health and disease: http://biobase.dk/cgi-bin/celis. FEBS Lett. 398: 129-134.

Cevc G., Gebauer D., Stieber J., Schatzlein A., Blume G. (1998) Ultraflexible vesicles, Transfersomes, have an extremely low pore penetration resistance and transport therapeutic amounts of insulin across the intact mammalian skin. Biochim Biophys Acta 1368: 201-215.

Christiansen O.B., Kilpatrick D.C., Souter V., Varming K., Thiel S., Jensenius J.C. (1999) Mannan-binding lectin deficiency is associated with unexplained recurrent miscarriage. Scand J Imrnunol 49: 193-196.

Corder E.H., Saunders A.M., Strittmatter W.J., Schmechel D.E., Gaskell P.C., Small G.W., Roses A.D., Haines J.L., Pericak-Vance M.A. (1993) Gene dose of apolipoprotein E type 4 allele and the risk of Alzheimer's disease in late onset families. Science 261: 921-923.

Costa P., Checkoway H., Levy D., Smith-Weller T., Franklin G.M., Swanson P.D., Costa L.G. (1997) Association of a polymorphism in intron 13 of the monoamine oxidase Bgene with Parkinson disease. Am. J. Med. Genet. 74:154-156.

Croake J.W., Pursley M., Hardin J.G., Michalski J.P. (1998) Systemic lupus erythromatosus and dementia. Psychol. Rep. 83; 1038.

Davidsson PI, Westman A., Puchades M., Nilsson C.L., Blennow K. (1999) Characterization of Proteins from Human Cerebrospinal Fluid by a Combination of Preparative Two-Dimensional Liquid-Phase Electrophoresis and Matrix-Assisted Laser Desorption/Ionization Time-of-Flight Mass Spectrometry, Anal. Chem. 71: 642-647.

Delacourte A., David J.P., Seargeant N., Buee L., Wattez A., Vermersch P., Ghozali F., Fallet-Bianco C., Pasquier F., Lebert F., Petit H., Di Menza C. (1999) The biochemical pathway of neurofribillary degeneration in aging and Alzheimer's disease. Neurology 52: 1158-1165.

den Dunnen J.T., Antonarakis S.E. (2000) Mutation nomenclature extensions and suggestions to describe complex mutations: A discussion. Hum. Mutat. 15: 7-12.

Feinglass E.J., Arnett F.C., Dorsch C.A., Zizic T.M., Stevens M.B. (1989) Neuropsychiatric manifestations of systemic lupus erythromatosus: diagnosis, clinical spectrum, and relationship to other features of the disease. Medicine (Baltimore) 68: 1034.

Finckh U., Muller-Thomsen T., Mann U., Eggers C., Marksteiner J., Meins W., Binetti G., Alberici A., Hock C., Nitsch R.M., Gal A. (2000) High prevalence of pathogenic mutations in patients with early-onset dementia detected by sequence analyses of four different genes. Am. J. Hum. Genet. 66: 110-117.

Garred P., Pressler T., Lanng S., Madsen H.O., Moser C., Laursen 1., Balstrup F., Koch C., Koch C. (2002) Mannose-binding lectin (MBL) therapy in an MBLdeficient patient with severe cystic fibrosis lung disease. Pediatr. Pulmonol. 33: 201207.

Garred P., Larsen F., Madsen H.O., Koch C. (2003) deficiency—revisited. Review. Mol. Immunol. 40: 73-84 Mannose-binding lectin.

Glenn G.M., Rao M., Matyas G.R., Alving C.R. (1998) Skin immunization made possible by cholera toxin. Nature 391: 851.

Gut I.G. (2001) Automation in genotyping of single nucleotide polymorphisms. Hum. Mutat. 17: 475-492.

Hanly J.G., Liang M.H. (1997) Cognitive disorders in systemic lupus erythematosus. Epidemiologic and clinical issues. Review. Ann. N.Y. Acad. Sci. 823: 60-68.

Hansen S., Holmskov U. (1998) Structural aspects of collectins and receptors for collectins. Immunobiology 199: 165-189.

Higgins G.A., Large C.H., Rupniak H.T., Barnes J.C. (1997) Apolipoprotein E and Alzheimer's disease: a review of recent studies. Review. Pharmacol. Biochem. Behav. 56: 675-85.

Hoda F., Nicholl D., Bennett P., Arranz M., Aitchison K.J., al-Chalabi A., Kunugi H., Vallada H., Leigh P.N., Chaudhuri K.R., Collier D.A. (1996) No association between Parkinson's disease and low-activity alleles of catechol O-methyltransferase. Biochem. Biophys. Res. Commun. 228: 780-784.

Hotamisligil G.S., Girmen A.S., Fink J.S., Tivol E., Shalish C., Trofatter J., Baenziger J., Diamond S., Markham C., Sullivan J., et al. (1994) Hereditary variations in monoamine oxidase as a risk factor for Parkinson's disease. Mov. Disord. 9: 305-310.

IFCC. (1987) Approved recommendation (1987) on the theory of reference values. Part. 5. Statistical treatment ofcollected refereece values. Determination of reference limits. Clinica Chimica Acta 170:S13-S32.

Jensenius J.C., Jensen P.H., McGuire K., Larsen J.L., Thiel S. (2003) Recombinant mannan-binding lectin (MBL) for therapy. Biochem. Soc. Trans.31(Pt 4):763-767.

Katzmann R., Fox P.J. (1999) The world-wide impact of dementia. Projections of prevalence and costs. In: Mayeux R., Christen Y. (eds.) Epidemiology of Alzheimer's disease: From gene to prevention. Research and perspectives in Alzheimer's disease. Berlin: Springer-Verlag, pp. 1-17.

Kilpatrick D.C. (2002a) Mannan-binding lectin: clinical significance and applications. Biochimica et Biophysica Acta 1572: 401-413.

Kilpatrick D.C. (2002b) Mannan-binding lectin and its role in innate immunity. Transfusion Medicine 12: 335-351.

Klose J., Kobalz U. (1995) Two-dimensional electrophoresis of proteins: an updated protocol and implications for a functional analysis of the genome. Electrophoresis 16: 1034-1059.

Kuhlman M., Joiner K., Ezekowitz R.A. (1989) The human mannose-binding protein functions as an opsonin. J. Exp. Med. 169: 1733-1745.

Kurth J.H., Kurth M.C., Poduslo S.E., Schwankhaus J.D. (1993) Association of a monoamine oxidase B allele with Parkinson's disease. Ann. Neurol. 33: 368-372.

Lambert J.C., Berr C., Pasquier F., Delacourte A., Frigard B., Cottel DPerez-Tur J., Mouroux Y., Mohr M., Cecyre D., Galasko D., Lendon C., Poirier J., Hardy J., Mann D., Amouel P., Chartier-Harlin M.C. (1998) Pronounced impact of Th1/E47cs mutation compared with -491 AT mutation on neural APOE gene expression and risk of developing Alzheimer's disease. Hum. Mol. Genet. 7: 1511-1516.

Lambert J.C., Pasquier FI, Cottel D., Frigard B., Amouyel P., Chartier-Harlin M.C. (1998b) A new polymorphism in the APE promoter associated with risk of developing Alzheimer's disease. Hum. Mol. Genet. 7: 533-540.

Langer R. (1990) New methods of drug delivery. Science 249: 1527-1533.

Langer R., Cleland J.L., Hanes J. (1997) New advances in microsphere-based singledose vaccines. Adv. Drug Deliv. Rev. 28: 97-119.

Launer L.J, Andersen K., Dewey M.E., Letenneur L., Ott A., Amaducci L.A., Brayne C., Copeland J.R., Dartigues J.-F., Kragh-Sorensen P., Lobo A., Martinez-Lage J.M., Stijnen T., Hofman A. (1999) Rates and risk factors for dementia and Alzheimer's disease: results from EURODEM pooled analyses. EURODEM Incidence Research Group and Work Groups. European Studies of Dementia. Neurology 52: 78-84.

Le Couteur D.G., Leighton P.W., McCann S.J., Pond S. (1997) Association of a polymorphism in the dopamine-transporter gene with Parkinson's disease. Mov. Disord. 12: 760-763.

Lwin A., Orvisky E., Goker-Alpan 0., LaMarca M.E., Sidransky E. (2004) Glucocerebrosidase mutations in subjects with parkinsonism. Mol. Genet. Metab. 81: 70-73.

Madsen H.O., Garred P., Kurtzhals L.A., Lamm L.V., Ryder L.P., Thiel S., Svejgaard A. (1994) A new frequent allele is the missing link in the structural polymorphism of the human mannan-binding protein. Immunogenetics 40: 37-44.

Madsen H.O., Garred P., Thiel S., Kurtzhals L.A., Lamm L.V., Ryder L.P., Svejgaard A. (1995) Interplay between promoter and structural gene variants control basal serum level of mannan-binding protein. J. Immunol. 155: 3013-3020.

McCune W.I., Golbus I. (1988) Neuropsychiatric IUpus. Review. Rheum. Dis. Clin. North. Am. 14: 149-167.

McGee J.P., Singh M., Li X.M., Qiu H., O'Hagan D.T. (1997) The encapsulation of a model protein in poly (0, L lactide-co-glycolide) microparticles of various sizes: an evaluation of process reproducibility. J. Microencapsul. 14: 197-210.

McKhann G., Drachman D.A., Folstein M.F., Katzman R., Price D.L., Stadlan E. (1984) Clinical diagnosis of Alzheimer's disease: report of the NINCDS-ADRDA Work Group under the auspices of the Department of Health and Human Services Task Force on Alzheimer's disease. Neurology 34: 939-944.

Miller M.E., Seals J., Kaye R., Levitsky L.C. (1968) A familial plasma associated defect of phagocytosis. The Lancet 292 (7559): 60-63.

Minchinton R.M., Dean M.M, Clark T.R., Heatley S., Mullighan C.G. (2002) Analysis of the relationship between mannose-binding lectin (MBL) genotype, MBL levels and function in an Australian blood donor population. Scand. J. Immunol. 56: 630-641.

Monroe et al. (1986) Liposome Immunoassay: A New Ultrasensitive Analytical Method. Amer. Clin. Prod. Rev. 5: 34-41.

Mui S., Briggs M., Chung H., Wallace R.B., Gomez-Isla T., Rebeck G.W., Hyman B.T. (1996) A newly identified polymorphism in the apolipoprotein E enhancer gene region is associated with Alzheimer's disease and strongly with the epsilon 4 allele. Neurology 47: 196-20I.

Nanko S., Ueki A., Hattori M., Dai X.Y., Sasaki T., Fukuda R., Ikeda K., Kazamatsuri H. (1994) No allelic association between Parkinson's disease and dopamine D2, D3, and D4 receptor gene polymorphisms. Am. J. Med. Genet. 154: 361-364.

Nanko S., Ueki A., Hattori M. (1996) No association between Parkinson's disease and monoamine oxidase A and B gene polymorphisms. Neurosci. Lett. 204: 125-127.

O'Farrell P.H. (1975) High resolution two-dimensional electrophoresis of proteins. J Biol. Chem. 250: 4007-4021.

Papassotiropoulos A., Streffer J.R, Tsolaki M., Schmid S., Thal D., Nicosia F., Iakovidou V., Maddalena A., Lutjohann D., Ghebremedhin E., Hegi T., Pasch T., Traxler M., Bruhl A., Benussi L., Binetti G., Braak H., Nitsch RM., Hock C. (2003) Increased brain beta-amyloid load, phosphorylated tau, and risk of Alzheimer disease associated with an intronic CYP46 polymorphism. Arch. Neurol. 60: 29-35.

Patterson S.D., Aebersold R (1995) Mass spectrometric approaches for the identification of gel-separated proteins. Electrophoresis 16: 1791-814.

Paul A., Cevc G., Bachhawat B.K. (1995) Transdermal immunization with large proteins by means of ultra deformable drug carriers. Eur. J. Immunol. 25: 3521-3524.

Plante-Bordeneuve V., Taussig D., Thomas F., Said G., Wood N.W., Marsden C.D., Harding A.E. (1997) Evaluation of four candidate genes encoding proteins of the dopamine pathway in familial and sporadic Parkinson's disease: evidence for association of a DRD2 allele. Neurology 48: 1589-1593.

Radebaugh T.S., Ganguli M., Khachaturian Z.D. (1999) Heterogeneity in Alzheimer's disease: implications for epidemiology. Berlin: Springer Verlag, pp. 41-47.

Roses A.D. (1996) Apolipoprotein E alleles as risk factors in Alzheimer's disease. Review. Annu. Rev. Med. 47: 387-400.

Seelen M.A., Wieslander J.W., Sommarin Y., Persson A., Schlagwein N., Daha M.R., Roos A., the European Workgroup on Complement in Disease. Functional assays for the assessment of the activity of the three pathways of complement activation in a simple ELISA format. Mol. Immunol. (Special Issue: 9th European Complement Workshop, Sep. 6-9, 2003, Trieste, Italy) vol. 40: 194-195 (Abstract).

Seelen M.A., Roos A., Wieslander J., Mollnes T.E., Sjoholm A.G., Wurzner R., Loos M., Tedesco F., Sim R.B., Garred P., Alexopoulos E., Turner M.W., Daha M.R (2005) Functional analysis of the classical, alternative, and MBL pathways of the complement system: standardization and validation of a simple ELISA. J. Immunol. Methods 296: 187-198.

Stefanovic M., Topic E., Ivanisevic A.M., Relja M., Korsic M. (2000) Genotyping of CYP2D6 in Parkinson's disease. Clin. Chem. Lab. Med. 38: 929-934.

Steffensen R, Thiel S., Vamling K., Jersild C., Jensenius J.C. (2000) Detection of structural gene mutations and promoter polymorphisms in the mannan-binding lectin (MBL) gene by polymerase chain reaction with sequence-specific primers. J. Immunol. Methods 241: 33-42.

Steffensen R., Hoffinann K., Varming K. (2003) Rapid genotyping of MBL2 gene mutations using real-time PCR with fluorescent hybridization probes. J. Immunol. Methods. 278: 191-199.

Stuyver L., Wyseur A., van Arnhem W., Hernandez F., Maertens G. (1996) A second generation line probe assay for hepatitis C virus. J. Clin. Microbiol. 34: 2259-2266.

Stuyver L., Wyseur A., Rombout A., Louwagie J., Scarcez T., Verhofstede C., Rimland D., Schinazi R.F., Rossau R (1997) Line probe assay (LiPA) for the rapid detection of drug-selected mutations in the human immunodeficiency virus type 1 reverse transcriptase gene. Antimicrob. Agents Chemother. 41: 284-291.

Sullivan K.E., Wooten C., Goldman D., Petri M. (1996) Mannose-binding protein genetic polymorphisms in black patients with systemic lupus erythematosus. Arthritis Rheum. 39: 2046-2051.

Super M., Thiel S., Lu J., Levinsky R.J., Turner M.W. (1989) Association of low levels of mannan-binding protein with a common defect of opsonisation. The Lancet 334 (8674): 1236-1239.

Super M., Levinsky R.J., Turner M.W. (1990) The level of mannan-binding protein regulates the binding of complement-derived opsonins to rnannan and zymosan at low serum concentrations. Clin. Exp. Immunol.79: 144-150.

Syvanen A.G. (2001) Accessing genetic variation: genotyping single nucleotide polyrnorphisms. Nat. Rev. Genet. 2: 930-942.

Tsai M.S., Tangalos E.G., Petersen R.C., Smith G.E., Schaid DJ., Kokmen E., Ivnik R.J., Thibodeau S.N. (1994) Apolipoprotein E: risk factor for Alzheimer disease. Am. J. Hum. Genet. 54: 643-649.

Turner M.W. and Harnvas R.M.J. (2000) Mannose-binding lectin: structure, function, genetics and disease associations. Rev. Immunogenetics 2: 305-322.

Turner M.W. (2003) Review. The role of mannose-binding lectin in health and disease. Mol Imrnunol. 40: 423-429.

Valdimarsson H., Stefansson M., Vikingsdottir T., Arason G.J., Koch c., Thiel S., Jensenius J.C. (1998) Reconstitution of opsonizing activity by infusion of mannanbinding lectin (MBL) to MBL-deficient humans. Scand. J. Immunol. 48: 116-123.

Valdimarsson H. (2003) Infusion of plasma-derived mannan-binding lectin (MBL) into MBL-deficient humans. Biochem. Soc. Trans.31 (Pt 4): 768-769.

Van Geyt C., De Gendt S., Rombaut A., Wyseur A., Maertens G., Rossau R., Stuyver L. (1998) A line probe assay for hepatitis B virus genotypes. In: R.F. Schinazi, J.P. Sommadossi, and H. Thomas (eds.). Therapies of viral hepatitis. International Medical Press, London, UK, pp. 139-145.

Wragg M., Hutton M., Talbot C. (1996) Genetic association between intronic polymorphism in presenilin-1 gene and late-onset Alzheimer's disease. Alzheimer's Disease Collaborative Group. Lancet 347 (9000):: 509-512.

Xiao W., Brandsma J.L. (1996) High efficiency, long-term clinical expression of cottontail rabbit papillomavirus (CRPV) DNA in rabbit skin following particlemediated DNA transfer. Nucleic Acids Res. 24: 2620-2622.

Yan J.X., Tonella L., Sanchez J.C., Wilkins M.R., Packer N. H., Gooley A.A., Hochstrasser D.F., Williams K.L. (1997) The *Dictyostelium discoideum* proteome-the SWISS-2DPAGE database of the multicellular aggregate (slug). Electrophoresis 18: 491-497.

Yokota Y., Arai T., Kawasaki T. (1995) Oligomeric structures required for 15 complement activation of serum mannan-binding proteins. J. Biochem. 117: 414-419.

Zhao L.P., Li S.S., Khalid, N. (2003) A Method for the assessment of disease associations with single-nucleotide polymorphism haplotypes and environmental variables in case-control studies. American Journal of Human Genetics 72: 123120 1250.

International Search Report mailed Dec. 6, 2005, for co-pending International Application PCT/EP2005/050772.

Extended European Search Report mailed Aug. 26, 2004 for co-pending European Application No. 04447050.

European Search Report mailed Jul. 14, 2008 for co-pending European Application No. 05708052.

* cited by examiner

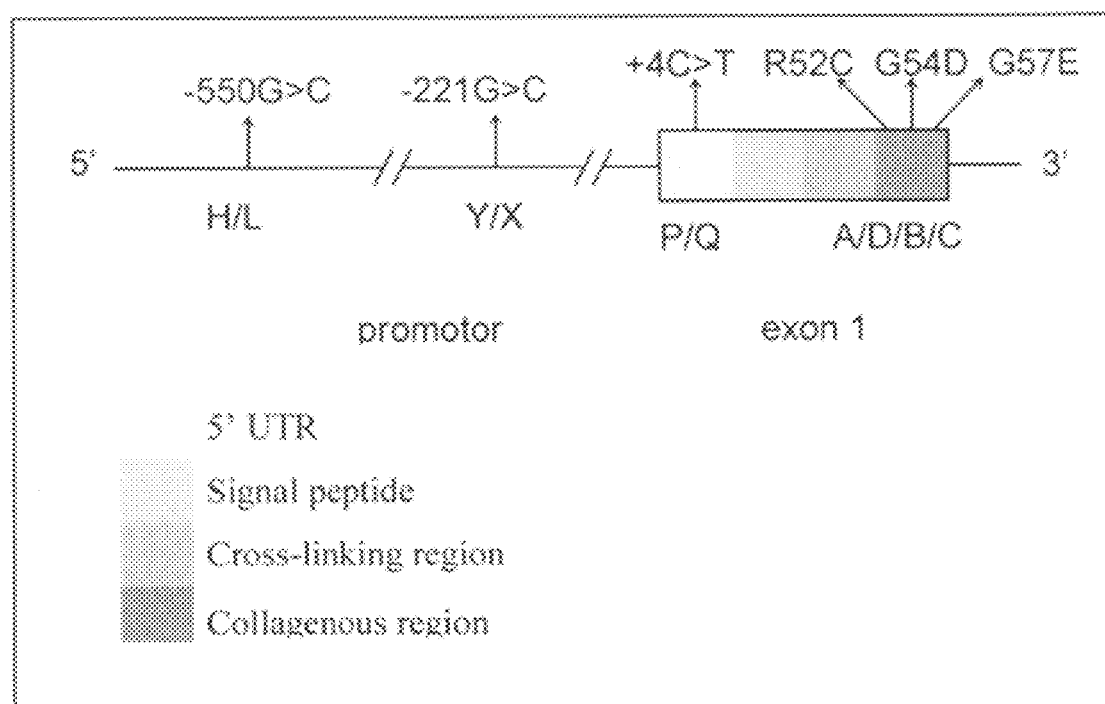

METHOD FOR DETERMINING THE RISK OF DEVELOPING A NEUROLOGICAL DISEASE

This application is a continuation of U.S. Application Ser. No. 11/063,716, filed Feb. 23, 2005 now abandoned, which claims benefit of priority to EP 04447050.8, filed Feb. 24, 2004; U.S. Provisional Application No. 60/552,847, filed Mar. 12, 2004; and EP 04103052.9, filed Jun. 29, 2004, each of which is herein incorporated by reference in its entirety.

FIELD OF THE INVENTION

The present invention relates to the field of diagnosis of neurological diseases. More particularly, the present invention provides a method for determining the risk of developing a neurological disease, such as Alzheimer's disease or multiple sclerosis. The method of the invention is based on the detection of the presence or absence of one or more nucleic acid variants in the MBL genes of the subject under diagnosis.

BACKGROUND ART

Mannan-binding lectin (MBL) is a plasma collectin (protein with both collagen-like and C-type lectin domains) synthesised by hepatocytes and secreted into the blood stream. MBL is thought to have an important role in the innate immune system via the MBL pathway of complement activation. MBL is a multimeric molecule that can bind to a wide variety of bacteria and other microbes, neutralising them and/or opsonizing them by activating complement using the lectin pathway of complement activation. MBL binds to repeating mannose and N-acetylglucosamine sugar motifs characteristically displayed in high density on bacteria, fungi, viruses and protozoa but not on mammalian cells (Minchinton et al., 2002). It has been suggested that MBL plays an important role in the first hours/days of any primary immune response to a sugar-decorated pathogen. This provides the host with a first-line of defence before the adaptive immune system becomes operative. In addition, in humans MBL may be particularly important between 6 and 18 months of age when the adaptive system is still immature.

The human collectin genes are all located in a cluster on chromosome 10 (q21-24) (Hansen and Holmskov, 1998). There are two human MBL genes, MBL-1 a pseudogene and MBL-2 which encodes a protein product. MBL-2 comprises four exons with exon 1 (FIGURE) encoding a signal peptide, a cysteine-rich region and part of the glycine-rich collagenous region. Exon 2 encodes the remainder of the collagenous region and exon 3 encodes an a-helical coiled-coil structure that is known as the 'neck' region. The fourth exon encodes the carbohydrate-recognition domain that adopts a globular configuration.

MBL deficiency has been reported in many different populations and is largely explained by three structural and three promoter mutations. The structural mutations occur at high frequency (generally 15% or greater cumulative allele frequency in most population studies) and are single base changes in codons 52, 54 and 57 of exon 1 (nucleotides +154, +161 and +170 respectively). The changes are: Arg-52 to Cys (R52C, MBL D variant), Gly-54 to Asp (G54D, MBL B variant) and Gly-57 to Glu (G57E, MBL C variant). The A variant is wild-type MBL and O refers to all the variants combined (Madsen et al., 1994; 1995). The B and C variants have disrupted Gly-$Xaa_1$-$Xaa_2$ repeats of the collagenous region resulting in an altered capacity to form the collagen triple helix. The D variant introduces an additional cysteine residue and so may disrupt oligomer formation by generation of additional disulphide bands. The B variant mutation occurs in 22-28% of Eurasian populations, whereas the C variant mutation is characteristic of sub-Saharan African populations in whom it reaches frequencies of 50-60%. The D mutation reaches frequencies of 14% in European populations but can be much lower elsewhere.

In addition to the above structural gene mutations, several polymorphisms have been described in the promoter region and the 5' UTR of the MBL gene (Madsen et al., 1995). These are the H/L, Y/X and P/Q loci at positions −550, −221 and +4 respectively of the MBL gene. The three loci are closely linked and four promoter haplotypes (LXP, LYP, LYQ and HYP) are commonly found.

Due to linkage disequilibrium, only seven haplotypes: HYPA, LYPA, LYQA, LXPA, LYPB, LYQC, and HYPD are commonly found (Minchinton et al, 2002). Two other very rare haplotypes have been described: HXPA in three African-American patients with systemic lupus erythematosus (Sullivan et al., 1996) and LYPD recently found in an Euro-Brazilian individual (Boldt and Petzl-Erler, 2002).

The concentration of MBL2 in serum is highly variable between healthy individuals. This variation is highly genetically determined by the presence of promoter, 5' UTR and exon 1 polymorphisms. Previous studies have indicated that the three structural variants B, C, and D and some of the promoter haplotypes have a dominant effect on the MBL concentrations in serum. Genotypes made up of combinations of seven haplotypes are mainly responsible for a 1000-fold concentration variation found in healthy human beings. All three exon 1 variants are associated with significantly decreased MBL levels compared with homozygotes of the wild-type gene. For example, the relatively common A/B heterozygotes generally have around a tenth of the MBL concentration found in A/A individuals, while B/B homozygotes or compound variant heterozygotes (B/C, etc.) typically possess MBL levels around the limit of detection by enzyme linked immunosorbent assay (ELISA) methods. These variant structural alterations cause a disruption in initiating the collagen formation as. such, preventing proper trimer formation resulting in a non-functional MBL2 peptide. These structural abnormal peptide chains are shown to render MBL more susceptible to matrix metalloproteinase proteolysis resulting in diminished MBL2 measurable in serum. The dimorphic H/L and Y/X loci allow modulation at the transcriptional level, with associated production H>L and Y>X (Kilpatrick, 2002a). It has been well established that high MBL2 producing haplotypes are HYP, followed by LYQ and LYP, whereas the LXP haplotype is associated with the lowest level of serum MBL2. The LX promoter is shown to have an influence on the MBL2 level similar to that found in individuals with the B structural gene variant (Steffensen et al., 2000).

Several studies have shown that deficiency of soluble MBL2 in the bloodstream increases the overall susceptibility of an individual to infection and may constitute a significant risk factor when immunity is co-compromised. Several independent reports have shown that low MBL2 concentrations are involved in recurrent infections, especially in children and immunocompromised individuals such as cancer patients undergoing chemotherapy. Furthermore, MBL2 can affect the course of autoimmune diseases, cystic fibrosis, and is possibly implicated in recurrent miscarriage. The role of MBL2 in immunodeficiency virus (HIV) infection has attracted much attention and has resulted in somewhat conflicting findings. The role of MBL2 in relation to viral hepatitis is also under debate. In general, chronic infection with either hepatitis B or hepatitis C virus was generally associated with lowered MBL (Kilpatrick, 2002a).

In contrast, there is evidence that for some intracellular parasites such as *Leishmania*, MBL deficiency may be protective and this might explain the high frequency of MBL mutations in sub-Saharan Africa and South America.

Increasingly, there is evidence that the association between MBL levels and disease is complex. A number of publications have now appeared which suggest that MBL is also able to modulate disease severity in both infectious and autoimmune disease (Turner, 2003). The mechanism whereby MBL exerts such effects is unclear but one possibility is through a dose-dependent modulation of pro-inflammatory cytokines. Lanzrein et al. (1998) observed a lowered level of MBL2 in the CSF of Alzheimer's disease (AD) patients compared to control subjects. Since the serum levels of MBL2 were not changed in the same patients, this reduction of MBL2 in CSF appears to be linked to a higher degree of MBL consumption connected with complement activation in AD patients. So far, no genetic association studies with MBL have been reported in AD or other neurological diseases.

Alzheimer's disease (AD) is an age-related, progressive neurodegenerative disorder characterised by irreversible cognitive and physical deterioration. The incidence of AD increases with age, affecting 1 out of 10 persons older than age 65 and nearly 1 out of 2 persons older than age 85. Overall, the natural history of the disease can be characterised as an irreversibly progressive brain disorder that ultimately results in devastating memory loss, profound behavioural and personality changes, and severely damaged cognitive abilities. These impairments are related to the underlying death of brain cells and the breakdown of communication between them. In view of the large expenses for health care systems that must provide institutional and ancillary care for the AD patients, the impact of AD on society and on national economies is enormous.

Epidemiological studies have demonstrated several known or potential risk factors in AD, including advanced chronological age, female gender, low education level and positive family history of dementia (Alloul et al., 1998; Katzmann and Fox, 1999; Radebaugh et al., 1999; Launer et al., 1999). Of the different genetic markers identified, the most important risk factor to date is Apolipoprotein E (Apo E). The ε4 allele is recognised as a susceptibility gene for early-and late-onset familial AD as well as for sporadic AD (Corder et al., 1993; Tsai et al., 1994; Roses, 1996; Higgins et al., 1997). More recently, other polymorphisms in the promoter region of the Apo E gene have been found to be associated with AD (Mui et al., 1996; Artiga et al., 1998; Lambert et al., 1998a; b). In autosomal dominant early-onset AD, mutations in 3 additional genes have been identified, the amyloid precursor protein (APP), presenilin 1 (PSEN1), and presenilin 2 (PSEN2) genes (Campion et al., 1999; Finckh et al., 2000). The presenilin-1 (PSEN1) genotype and a CYP46 polymorphism have also been associated with a higher risk of late-onset sporadic AD (Wragg et al., 1996; Papassotiropoulos et al., 2003). The relative contribution of APP, PSEN and CYP46 mutations is, however, the subject of considerable controversy and the involvement of other genetic factors is suggested.

Multiple sclerosis (MS) is an inflammatory disease of the central nervous system (CNS). Predominantly, it is a disease of the white matter tissue. In people affected by MS, patches of damage called plaques or lesions appear in seemingly random areas of the CNS white matter. At the site of a lesion, a nerve insulating material, called myelin is lost (i.e. demyelination). People with MS can experience partial or complete loss of any function that is controlled by, or passes through, the brain or spinal cord.

The most obvious risk factor for MS is gender (female sex). In all studies, MS affects women more than men. Other risk factors include ethnicity (MS is most common in Caucasian people of northern European origin and extremely rare among Asians, Africans and Native Americans) and family history. People who have relatives with MS are more likely to develop the disease than people with no family history of MS. It seems clear from various population studies that there is a genetic susceptibility involved in contracting the disease.

Several other neurological disease have been associated with certain genetic risk factors. Dementia with Lewy bodies (DLB), for example, is an illness that presents with progressive dementia or psychosis. Parkinsonian signs, which may be absent or mild at the onset, eventually become common and rigidity is usually severe. Lewy bodies are found profusely in the brainstem, basal forebrain, hypothalamic nuclei and neocortex. Dementia with Lewy bodies is characterized by the relative absence of tangles and hyperphosphorylated tau in the brain. Parkinson's disease (PD) is a type of Lewy Body disease occurring in the middle or late life, with very gradual progression and a prolonged course. It can be considered as an example of neuronal system disease, involving mainly the nigrostriatal dopaminergic system. Elevated frequencies of the common CYP2D6 mutant allele, CYP2D6B, have been found among PD patients compared to controls, with an approximate doubling of risk for subjects homozygous or heterozygous for this allele (Armstrong et al., 1992; Stefanovic et al., 2000). Several other genetic markers have been variably associated with PD such as glucocerebrosidase ( Lwin et al., 2004), monoamine oxidase A (Hotamisligil et al., 1994; Nanko et al., 1996), monoamine oxidase B (Kurth et al., 1993; Costa et al., 1997), dopamine receptors and transporters (Nanko et al., 1994; Le Couteur et al., 1997; Plante-Bordeneuve et al., 1997), and catechol-O-methyl transferase (Hoda et al., 1996). Despite these different associations of genetic risk factors with certain neurological diseases, there is a continuous search toward more accurate genetic markers that provide a reliable prediction of the risk to develop a neurological disease.

SUMMARY OF THE INVENTION

The present invention provides methods and kits for determining whether a subject is at risk (has an enhanced or elevated risk) of developing a neurological disease. The methods and kits of the invention are based on the detection of the presence or absence of one or more nucleic acid variants in the MBL genes of said subject. Based on the presence or absence of certain nucleic acid variants in said genes, it can be determined whether the subject is at risk of developing a neurological disease.

The methods and kits of the present invention particularly relate to the detection of nucleic acid variant sequences in the promoter region, in the 5' untranslated region (5' UTR) and in exon 1 of the MBL2 genes. More particularly, the present invention relates to the detection of nucleic acid variant sequences in the MBL2 genes at the nucleic acid positions −550, −221, +4, +154, +161 and/or +170. In a preferred embodiment of the invention, following nucleic acid variant sequences are detected in the MBL2 gene at positions −550 (G>C), −221 (G>C), +4 (C>T), +154 (C>T), +161 (G>A) and/or +170 (G>A). In another preferred embodiment of the invention, following nucleic acid variant sequences are detected in the MBL2 genes at positions −221 (G>C), +154 (C>T), +161 (G>A) and/or +170 (G>A).

The prevalence of the nucleotide T at position +154 (variant D), nucleotide A at position +161 (variant B) and nucleotide A at position +170 (variant C) of the MBL2 genes appeared to be much lower in subjects suffering from AD compared to subjects in a control group. Accordingly, the absence of the nucleotide T at position +154 (variant D), nucleotide A at position +161 (variant B) and nucleotide A at position +170 (variant C), or the absence of the haplotypes HYPD, LYPB and LYQC, indicates that the subject is at risk of developing a neurological disease such as Alzheimer's disease.

The prevalence of the nucleotide C at position −221 (variant X) of the MBL2 genes appeared to be much higher in subjects suffering from AD compared to subjects in a control group. Accordingly, the presence of nucleotide C at position −221 (variant X), or the presence of the haplotype LXPA indicates that the subject is at risk of developing a neurological disease such as Alzheimer's disease.

The prevalence of the LYPA haplotype appeared to be higher in subjects suffering from MS compared to subjects in a control group. Accordingly, the presence of the haplotype LYPA indicates that the subject is at risk of developing a neurological disease such as multiple sclerosis.

The nucleic acid variants in the MBL genes can also be detected by their phenotype. Phenotypical detection includes the measurement of the concentration of one or more protein variants of the MBL product and/or measurement of the functional activity of the MBL product.

With the methods and kits of the present invention the risk for developing any neurological disease can be determined. In a preferred embodiment, the risk is determined for developing Alzheimer's disease, Pick's disease, Parkinson's disease, dementia with Lewy bodies, Huntington disease, chromosome 13 dementias, Down's syndrome, cerebrovascular disease, multiple sclerosis, Rasmussen's encephalitis, viral meningitis, neuropsychiatric system lupus erythematosus (NPSLE, McCune and Golbus, 1988; Feinglass et al., 1989; Hanly and Liang, 1997; Croake et al., 1998), amyotrophic lateral sclerosis, Creutzfeldt-Jacob disease, Gerstmann-Straussler-Scheinker disease, transmissible spongiform encephalopathies, ischemic reperfusion damage (e.g. stroke), brain trauma, microbial infection or chronic fatigue syndrome.

The methods and kits of the present invention can be carried out in vivo or in vitro. In a preferred embodiment, the methods and kits are carried out in vitro on a biological sample such as a tissue sample or a body fluid sample included but not limited to brain, blood, plasma, saliva, skin and cerebrospinal fluid.

The methods and kits of the present invention can also be carried out in combination with other methods for determining the risk of developing a neurological disease. In a preferred embodiment the methods and kits are carried out in combination with a method for Apo E genotyping and/or other markers.

FIGURE LEGENDS

FIGURE. Structure and organization of part of the MBL2 gene. The localization of the main polymorphisms is shown.

DETAILED DESCRIPTION OF THE INVENTION

The present invention relates to methods and kits for determining whether a subject is at risk of developing a neurological disease. The methods and kits of the invention are based on the detection of the presence or absence of one or more nucleic acid variants in the MBL genes of the subject. The present invention has identified that certain nucleic acid variants in the MBL genes are more frequently present in patients suffering from AD or MS compared to control subject while other nucleic acid variants in the MBL genes are more frequently absent in patients suffering from AD or MS compared to control subject. Accordingly, the present invention provides a method for determining whether a subject is at risk of developing a neurological disease, comprising:

(a) detecting the presence or absence of one or more nucleic acid variants in the MBL genes of said subject; and (b) determining, from the nucleic acid variants detected in step (a), whether the subject is at risk of developing a neurological disease, whereby the absence or presence of certain variant sequences in the MBL genes indicate that the subject is at risk of developing a neurological disease.

Nucleic acid variant sequences are preferably detected in the promoter region, in the 5' untranslated region (5' UTR), and/or in exon 1 of the MBL2 gene. More particularly, nucleic acid variant sequences in the MBL2 gene are detected at the nucleic acid positions −550, −221, +4, +154, +161 and/or +170. In a preferred embodiment of the invention, following nucleic acid variant sequences are detected in the MBL2 gene at positions −550 (G>C), −221 (G>C), +4 (C>T), +154 (C>T), +161 (G>A) and/or +170 (G>A). In another preferred embodiment of the invention, following nucleic acid variant sequences are detected in the MBL2 gene at positions −221 (G>C), +154 (C>T), +161 (G>A) and/or +170 (G>A).

Accordingly, the present invention provides a method for determining whether a subject is at risk of developing a neurological disease, comprising:

(a) detecting the presence or absence of one or more nucleic acid variants at positions −221 (G>C), +154 (C>T), +161 (G>A) and/or +170 (G>A) of the MBL2 genes of said subject; and (b) determining, from the nucleic acid variants detected in step (a), whether the subject is at risk of developing a neurological disease, whereby the absence or presence of certain variant sequences in the MBL2 genes indicates that the subject is at risk of developing a neurological disease.

More specifically, the present invention has identified that the prevalence of nucleotide T at position +154 (variant D), nucleotide A at position +161 (variant B) and nucleotide A at position +170 (variant C) of the MBL2 gene appeared to be much lower in subjects suffering from AD compared to subjects in a control group. Accordingly, the absence of nucleotide T at position +154 (variant D), nucleotide A at position +161 (variant B) and nucleotide A at position +170 (variant C), indicates that the subject is at risk of developing a neurological disease such as AD and the method of the invention comprises the following:

(a) detecting the presence or absence of one or more nucleic acid variants at positions +154 (nt T), +161 (nt A) and/or +170 (nt A) of the MBL2 genes of said subject; and (b) determining, from the nucleic acid variants detected in step (a), whether the subject is at risk of developing a neurological disease, whereby the absence of nucleotide T at position +154 (variant D), nucleotide A at position +161 (variant B) and nucleotide A at position +170 (variant C) of the MBL2 genes indicates that the subject is at risk of developing a neurological disease such as AD.

Nucleotide sequence T at position +154 (variant D), nucleotide A at position +161 (variant B) and nucleotide A at position +170 (variant C) correspond to the MBL2 haplotypes HYPD, LYPB and LYQC. Accordingly, the absence of the haplotypes HYPD, LYPB and LYQC indicates that the subject is at risk of developing a neurological disease such as AD.

The present invention has further identified that the prevalence of nucleotide C at position −221 (variant X) of the MBL2 gene appeared to be much higher in subjects suffering from AD compared to subjects in a control group. Accordingly, the presence of nucleotide C at position −221 (variant X) indicates that the subject is at risk of developing a neurological disease such as AD and the method of the invention comprises the following:
(a) detecting the presence or absence of a nucleic acid variant at position −221 of the MBL2 genes of said subject; and
(b) determining, from the nucleic acid variant detected in step (a), whether the subject is at risk of developing a neurological disease, whereby the presence of nucleotide C at position −221 (variant X) of the MBL2 genes indicates that the subject is at risk of developing a neurological disease such as AD.

Nucleotide sequence C at position −221 (variant X) corresponds to the MBL2 hapolotype LXPA. Accordingly, the presence of the haplotype LXPA indicates that the subject is at risk of developing a neurological disease such as AD.

The present invention has further identified that the prevalence of haplotype LYPA appeared higher in subjects suffering from MS compared to subjects in a control group. Accordingly, the presence of the haplotype LYPA indicates that the subject is at risk of developing a neurological disease such as MS and the method of the present invention comprises the following:
(a) detecting the MBL haplotype in said subject; and
(b) determining, from the haplotype detected in step (a), whether the subject is at risk of developing a neurological disease, whereby the presence of haplotype LYPA indicates that the subject is at risk of developing a neurological disease such as MS.

The term "nucleic acid" refers to a single stranded or double stranded nucleic acid sequence, which may contain from 8 nucleotides to the complete nucleotide sequence. A nucleic acid that is up to about 100 nucleotides in length, is often also referred to as an oligonucleotide. A nucleic acid may consist of deoxyribonucleotides or ribonucleotides, nucleotide analogues or modified nucleotides, or may have been adapted for therapeutic purposes.

The term "variant" or "nucleic acid variant" as used in the present invention, means that the nucleic acid sequence at a certain position in the MBL gene differs relative to one or more reference nucleic acid sequences (Genebank NM_000242.1 and NT_024082). The term "nucleic acid polymorphism" or "polymorphism" signifies the existence of two or more variants in the population present at a sequence of >1% of the population. The most simple nucleic acid polymorphism is a polymorphism affecting a single nucleotide, i.e. a single nucleotide polymorphism or SNP. Nucleic acid polymorphisms further include any number of contiguous and/or non-contiguous differences in the primary nucleotide sequence of the nucleic acid under investigation relative to the primary nucleotide sequence of one or more reference nucleic acids. The term "polymorphic position" or "position" refers to the nucleic acid position at which a nucleic acid polymorphism arises. Nucleic acid sequences comprising at least one such polymorphism are referred to as "polymorphic nucleic acid sequences", "polymorphic polynucleotides", "polymorphic sequences" or the like.

The term "haplotype" means a particular pattern of sequential polymorphisms found on a single chromosome. As used herein, the term "allele" is one of several alternative forms of a gene or DNA sequence at a specific chromosomal location (locus). At each autosomal locus an individual possesses two alleles, one inherited from the father and one from the mother.

The structure of part of the MBL2 gene, the gene encoding the human MBL protein, is shown in the FIGURE. The MBL2 gene has four exons. Exon 1 contains three single nucleotide polymorphisms:
at nucleic acid position 154 (C>T): codon 52 (R52C), referred to as "variant D";
at nucleic acid position 161 (G>A): codon 54 (G54D), referred to as "variant B";
at nucleic acid position 170 (G>A): codon 57 (G57E), referred to as "variant C"; while the wild type MBL2 gene is referred to as "variant A".

These polymorphisms each lead to a single amino acid substitution in the collagen-like domain causing some abnormality in its structure.

The promotor and 5' untranslated regions of the MBL2 gene are also polymorphic. Single nucleotide polymorphisms are present:
at nucleic acid position −550 (G>C): variants H/L;
at nucleic acid position −221 (G>C): variants Y/X;
at nucleic acid position +4 of the 5'UTR (C>T): variants P/Q.

Promotor variants are in absolute linkage desequilibrium with coding variants, and only seven of the 64 possible haplotypes have been observed, i.e. HYPA, LXPA, LYQA, LYPA, HYPD, LYPB and LYQC (Minchinton et al, 2002). Two other, rare haplotype have also been described: HXPA (Sullivan et al., 1996) and LYPD (Boldt and Petzl-Erler (2002).

The nomenclature for the MBL2 amino acid changes as used herein is generally accepted and recommended by den Dunnen and Antonarakis (2000). Frequent updates of the nomenclature for the description of sequence variations are provided on the web-site of the Human Genome Variation Society.

The subject on which the methods of the present invention is carried out can be any subject of which the risk for developing a neurological disease needs to be determined. The subject may be a non-human subject such as (but not limited to) a cow, a pig, a sheep, a goat, a horse, a monkey, a rabbit, a hare, a chicken, a dog, a cat, a mouse, a rat, a hamster, an elk, a deer, a tiger, an elephant, a zebrafish, a pufferfish (Fugu), a fly, a worm or C. elegans. More preferably, the subject is a primate. Even more preferably, the subject is a human.

With the methods of the present invention the risk for developing any neurological disease can be determined. Immune and inflammatory responses in the central nervous system (CNS) are observed in various chronic and acute neurological diseases such as Alzheimer's disease, myasthenia gravis, multiple sclerosis, microbial infections, head trauma and stroke, Pick's disease, Parkinson's disease, dementia with Lewy bodies, Huntington disease, chromosome 13 dementias, Down's syndrome, cerebrovascular disease, Rasmussen's encephalitis, viral meningitis, NPSLE, amyotrophic lateral sclerosis, Creutzfeldt-Jacob disease, Gerstmann-Straussler-Scheinker disease, transmissible spongiform encephalopathies, ischemic reperfusion damage. Therefore, in a preferred embodiment, the risk is determined for developing Alzheimer's disease, Pick's disease, Parkinson's disease, dementia with Lewy bodies, Huntington disease, chromosome 13 dementias, Down's syndrome, cerebrovascular disease, multiple sclerosis, Rasmussen's encephalitis, viral meningitis, NPSLE, amyotrophic lateral sclerosis, Creutzfeldt-Jacob disease, Gerstmann-Straussler-Scheinker disease, transmissible spongiform encephalopathies, ischemic reperfusion damage (e.g. stroke), brain trauma, microbial infection or chronic fatigue syndrome.

The term "developing a neurological disease" means that the subject, at the time that the method of the invention is carried out, does not show any clinical signs of a neurological disease, but that said subject will show clinical signs of a neurological disease later on during life time. The term "developing a neurological disease" may further implicate that the subject, at the time that the method of the invention is carried out, shows already clinical signs of a neurological disease. The method of the present invention is then carried out for the differential diagnosis of a neurological disease or for monitoring the course and severity of the disease progress. The terms "risk", "enhanced risk", "elevated risk" or "likelihood" are interchangeable and are used with respect to the probability of developing a neurological disease.

The method of the present invention can be carried out in vivo or in vitro. Preferred, however, is in vitro detection of nucleic acid variants in the MBL gene in a biological sample obtained from the subject. The term "biological sample" means a tissue sample or a body fluid sample. A tissue sample includes (but is not limited to) a brain sample, bucal cells or a skin sample. The term "body fluid" refers to all fluids that are present in the body including but not limited to blood, plasma, serum, lymph, urine, saliva or cerebrospinal fluid. The term "cerebrospinal fluid" or "CSF" is intended to include whole cerebrospinal fluid or derivatives of fractions thereof well known to those skilled in the art. Thus, a cerebrospinal fluid sample can include various fractionated forms of cerebrospinal fluid or can include various diluents added to facilitate storage or processing in a particular assay. The biological sample may also be obtained by subjecting it to a pretreatment if necessary, for example, by homogenizing or extracting. Such a pretreatment may be selected appropriately by those skilled in the art depending on the biological sample to be subjected.

A nucleic acid comprising an intended sequence prepared from a biological sample may be prepared from DNA or RNA. Release, concentration and isolation of the nucleic acids from the sample can be done by any method known in the art. Currently, various commercial kits are available such as the QIAamp Blood Kit from Qiagen (Hilden, Germany) for the isolation of nucleic acids from blood samples, or the 'High pure PCR Template Preparation Kit' (Roche Diagnostics, Basel, Switzerland). Other, well-known procedures for the isolation of DNA or RNA from a biological sample are also available (Sambrook et al., 1989).

When the quantity of the nucleic acid is low or insufficient for the assessment, the nucleic acid may be amplified. Such amplification procedures can be accomplished by those methods known in the art, including, for example, the polymerase chain reaction (PCR) and reverse transcription polymerase reaction (RT-PCR).

After performing the extraction and/or amplification procedure, the presence or absence of certain nucleic acid variants in the target sequence (the MBL gene) can be detected. Numerous methods for detecting a single nucleotide anomaly in nucleic acid sequences are well-known in the art. The present invention is not limited by any particular method used to detect the target sequences disclosed herein. Examples of such methods are described by Gut (2001) and Syvänen (2001), and include, but are not limited to, hybridization methods such as reverse dot blot, LiPA, genechip microarrays, DASH, PNA and LNA probes, TaqMan (5'nuclease assay) and molecular beacons; allele-specific PCR methods such as intercalating dye, FRET primers and Alphascreen; primer extension methods such as ARMS, kinetic PCR, SNP-stream, GBA, multiplex minisequencing, SNaPshot, pyrosequencing, MassExtend, MassArray, Goodassay, microarray miniseq, APEX, microarray primer extension, Tag arrays, coded microspheres, TDI, fluorescence polarization, oligonuceotide ligation methods such as colorimetric OLA, sequence-coded OLA, microarray ligation, ligase chain reaction, padlock probes and rolling circle amplification, endonuclease cleavage methods such as restriction site analysis (RFLP) and Invader assay. Possible MBL genotyping methodologies are also described in Turner et al. (2000), Steffensen (2000), Boldt and Petz-Erler (2002), Kilpatrick (2002b), Steffensen (2003) and Garred et al. (2003).

The presence of nucleic acid variants in the MBL genes of a subject may also be reflected phenotypically in the concentration, structure and functionality of the MBL product in, for example, the serum or plasma of said subject. Promoter mutations in the MBL2 gene are associated with a decreased production of MBL2. All three exon 1 variants are associated with a significant decrease of the concentration and functionality of the MBL2 level resulting in different protein variants. Therefore, the present invention also encompasses a method for determining whether a subject has a risk of developing a neurological disease wherein the nucleic acid variants in the MBL genes are detected by their phenotype. Phenotypic detection of nucleic acid variants in the MBL genes may encompass the measurement of one or more protein variants of the MBL product in said subject. Accordingly, the present invention relates to a method for determining whether a subject is at risk of developing a neurological disease, comprising:

(a) measuring the concentration of one or more protein variants of the MBL product;
(b) determining, from the measurement in step (a), whether the subject is at risk of developing a neurological disease, whereby a change in the concentration of a certain protein variant of MBL indicates that the subject is at risk of developing a neurological disease.

In a preferred embodiment, one or more protein variants of the MBL2 product are detected.

In another preferred embodiment, the method of the present invention comprises the following:

(a) measuring the concentration of the MBL2 protein variant with C at amino acid position 52 (variant D), D at amino acid position 54 (variant B) and/or E at amino acid position 57 (variant C); and
(b) determining, from the measurement in step (a), whether the subject is at risk of developing a neurological disease, whereby a decreased concentration of said MBL2 protein variants indicates that the subject is at risk of developing a neurological disease such as AD.

The term "concentration" or "level", as used in the present invention, refers to the presence or absence and/or amount of a certain protein variant. A change in the concentration of a protein variant refers to a measurable increase or decrease, including total absence or presence, in the protein variant concentration when compared to a control subject.

Phenotypic detection of nucleic acid variants in the MBL genes may also encompass the assessment of the MBL functional activity in said subject. Accordingly, the present invention relates to a method for determining whether a subject is at risk of developing a neurological disease, comprising:

(a) measuring the functional activity of the MBL product;
(b) determining, from the measurement in step (a), whether the subject is at risk of developing a neurological disease, whereby a change in the functional activity of the MBL product indicates that the subject is at risk of developing a neurological disease.

The "functional activity of the MBL product" or the "MBL functional activity" refers to the ability of the MBL product to initiate the MBL-dependent lectin pathway of complement (MBL pathway).

The above methods can be carried out in vivo or in vitro. Preferred, however, is in vitro detection of MBL protein variants or MBL functional activity in a biological sample (see above) obtained from the subject. In a preferred embodiment, the MBL protein variants or MBL functional activity are detected in the brain, blood, serum, plasma, tissue, bucal cells or CSF of said subject.

A "control subject", as defined in the present invention is a subject of the same species as the subject under examination which is free from, or not at risk of developing, the neurological disease. The concentration of any given protein variant or the functional activity of the MBL product obtained upon analyzing the subject under examination relative to the concentration or functional activity obtained upon analyzing a control subject will depend on the particular analytical protocol and detection technique that is used. Accordingly, those skilled in the art will understand that, based on the present description, any laboratory can establish, for a given MBL protein variant, a suitable "reference range", "reference level range", "concentration range or "range of levels" (those terms are used interchangeable) or a "reference functional activity" characteristic for control subjects according to the analytical protocol and detection technique in use. The concentration or functional activity obtained for the subject under examination can then be compared with this reference and based on this comparison, a conclusion can be drawn as to whether the subject has a risk of developing a neurological disease. Those skilled in the art will also know how to establish a cut-off value suitable for determining whether a subject is at risk of developing a neurological disease. Methods for defining cut-off values include (but are not limited to) the methods described by IFCC (1987).

The MBL products that are detected in the method of the present invention, may be detected by any method known to those skilled in the art. They can be identified by. their structure, by partial amino acid sequence determination, by functional assay, by enzyme assay, by various immunological methods, or by biochemical methods. The functional assay may encompass the measurement of the ability to opsonize heat-killed baker's yeast (Miller et al., 1968), the assessment of phagocytosis of various microorganisms (Kuhlman et al., 1989) and/or detection of complement activation (Super et al., 1989; 1990; Yokota et al., 1995). In a serum test for complement activation described by Seelen et al. (2003), for example, the lectin pathway function is assessed using plates coated with mannan, followed by incubation of the serum in buffer containing $Ca^{2+}$, $Mg^{2+}$ and an inhibitory antibody directed against C1q. The formation of the membrane attack complex is subsequently detected by use of a specific monoclonal antibody directed against C5b-9. More assays for the measurement of the functional activity of the MBL product are described by Seelen et al. (2005).

Biochemical methods include (but are not limited to) capillary electrophoresis, high performance liquid chromatography (HPLC), thin layer chromatography (TLC), hyperdiffusion chromatography, two-dimensional liquid phase electrophoresis (2-D-LPE; Davidsson et al. 1999) or detection of the migration pattern in gel electrophoreses. Sodium dodecyl sulfate-polyacrylamide gel electrophoresis (SDS-PAGE) is a widely used approach for separating proteins from complex mixtures (Patterson and Aebersold, 1995). It can be performed in one- or two-dimensional (2-D) configuration. For less complicated protein preparation, one-dimensional SDS-PAGE is preferred over 2-D gels, because it is simpler. However, SDS-PAGE often results in migrating or overlapping protein bands due to its limited resolving power. What appears to be a single band may actually be a mixture of different proteins. 2-D gel electrophoresis incorporates isoelectric focusing (IEF) in the first dimension and SDS-PAGE in the second dimension, leading to a separation by charge and size (O'Farrell, 1975). 2-D PAGE is a powerful technique for separating very complex protein preparations, resolving up to 10 000 proteins from mammalian tissues and other complex proteins (Klose and Kobalz, 1995; Celis et al., 1996; Yan et al., 1997).

The protein variants of MBL of the present invention can be identified by their isoelectric focusing point (pI) and their molecular weight (MW) in kilodaltons (kD).

As indicated above, the level of MBL protein variant can also be detected by an immunoassay. As used herein, an "immunoassay" is an assay that utilizes an antibody to specifically bind to the antigen (i.e. the MBL protein variant). The immunoassay is thus characterized by detection of specific binding of a MBL protein variant to an antibody. Immunoassays for detecting MBL protein variants may be either competitive or noncompetitive. Noncompetitive immunoassays are assays in which the amount of captured analyte (i.e. the MBL protein variant) is directly measured. In competitive assays, the amount of analyte (i.e. the MBL protein variant) present in the sample is measured indirectly by measuring the amount of an added (exogenous) analyte displaced (or competed away) from a capture agent (i.e. the antibody) by the analyte (i.e. the MBL protein variant) present in the sample. In one competition assay, a known amount of the (exogenous) MBL protein variant is added to the sample and the sample is then contacted with the antibody. The amount of added (exogenous) MBL protein variant bound to the antibody is inversely proportional to the concentration of the MBL protein variant in the sample before the exogenous MBL protein variant is added. In one preferred "sandwich" assay, for example, the antibodies can be bound directly to a solid substrate where they are immobilized. These immobilized antibodies then capture the MBL protein variant of interest present in the test sample. Other immunological methods include but are not limited to fluid or gel precipitation reactions, immunodiffusion (single or double), agglutination assays, immunoelectrophoresis, radioimmunoassays (RIA), enzyme-linked immunosorbent assays (ELISA), TRIFMA (Christiansen et al., 1999), Western blots, liposome immunoassays (Monroe et al., 1986), complement-fixation assays, immunoradiometric assays, fluorescent immunoassays, protein A immunoassays or immunoPCR. An overview of different immunoassays is given in Wild (2001), Ghindilis et al. (2002) and Kilpatrick (2002b).

In a preferred embodiment, the level of MBL protein variant is determined by an immunoassay comprising at least the following steps:
  (a) contacting the MBL protein variant with an antibody that specifically recognizes the MBL protein variant, under conditions suitable for producing an antigen-antibody complex; and
  (b) detecting the immunological binding that has occurred between the antibody and the MBL protein variant.

In another embodiment, the MBL protein variant can be detected by a sandwich ELISA comprising the following steps:
(a) bringing said MBL protein variant into contact with an antibody (primary antibody or capturing antibody) recognizing said MBL protein variant, under conditions being suitable for producing an antigen-antibody complex;
(b) bringing the complex formed between said MBL protein variant and said primary antibody into contact with another antibody (secondary antibody or detector antibody) specifically recognizing said MBL protein variant, under conditions being suitable for producing an antigen-antibody complex;
(c) bringing the antigen-antibody complex into contact with a marker either for specific tagging or coupling with said secondary antibody, with said marker being any possible marker known to the person skilled in the art;
(d) possibly also, for standardization purposes, bringing the antibodies in contact with a purified MBL protein variant reactive with both antibodies.

Advantageously, the secondary antibody itself carries a marker or a group for direct or indirect coupling with a marker.

The term "specifically recognizing", "specifically binding with", "specifically reacting with" or "specifically forming an immunological reaction with" refers to a binding reaction by the antibody to the MBL protein variant which is determinative of the presence of said MBL protein variant in the sample in the presence of a heterogeneous population of other proteins and/or other biologics. Thus, under the designated immunassay conditions, the specified antibody preferentially binds to a particular MBL protein variant while binding to other MBL protein variants and other proteins does not occur in significant amounts.

Any antibody that recognizes the MBL protein variant under examination can be used in the above method.

While various antibody fragments are defined in terms of enzymatic digestion of an intact antibody with papain, pepsin or other proteases, those skilled in the art will appreciate that such antibody fragments as well as full size antibodies may be synthesized either chemically or by utilizing recombinant DNA methodology. Thus, the term antibody, as used herein also includes antibodies and antibody fragments either produced by the modification of whole antibodies or synthesized using recombinant DNA methodologies. The humanized versions of the mouse monoclonal antibodies are also made by means of recombinant DNA technology, departing from the mouse and/or human genomic DNA sequences coding for H and L chains or from cDNA clones coding for H and L chains. Alternatively the monoclonal antibodies used in the method of the invention may be human monoclonal antibodies. The term 'humanized antibody' means that at least a portion of the framework regions of an immunoglobulin is derived from human immunoglobulin sequences.

The antibodies used in the method of the present invention may be labeled with an appropriate label. The particular label or detectable group used in the assay is not a critical aspect of the invention, so long as it does not significantly interfere with the specific binding of the antibody used in the assay. The detectable group can be any material having a detectable physical or chemical property. Such detectable labels have been well developed in the field of immunoassays and, in general, almost any label used in such methods can be applied to the method of the present invention. Thus, a label is any composition detectable by spectroscopic, photochemical, biochemical, immunochemical, electrical, radiological, optical, or chemical means. Useful labels in the present invention include, but are not limited to, magnetic beads (e.g. Dynabeads™), fluorescent dyes (e.g. fluorescein isothiocyanate, texas red, rhodamine), radiolabels (e.g. $^3$H, 125I, $^{35}$S, $^{14}$C, or $^{32}$P), enzymes (e.g. horseradish peroxidase, alkaline phosphatase, and others commonly used in an ELISA), and colorimetric labels such as colloidal gold, colored glass or plastic (e.g. polystyrene, polypropylene, latex, etc.) beads.

The label may be coupled directly or indirectly to the desired component or the assay according to methods well known in the art. As indicated above, a wide variety of labels may be used, with the choice of label depending on the sensitivity required, the ease of conjugation with the compound, stability requirements, the available instrumentation, and disposal provisions. Non-radioactive labels are often attached by indirect means. Generally, a ligand molecule (e.g. biotin) is covalently bound to the antibody. The ligand then binds to an anti-ligand (e.g. streptavidin) molecule, which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, a haptenic or antigenic compound can be used in combination with an antibody. The antibodies can also be conjugated directly to signal generating compounds, for example, by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umberlliferone, etc. Chemiluminescent compounds include luciferin, and 2,3-dihydrophthalazinediones, for example, luminol. A review of other labeling or signal producing systems is available in U.S. Pat. No. 4,391,904.

Means for detecting labels are well known in the art. Thus, for example, where the label is a radioactive label, means for detection include a scintillation counter or photographic film, as in autoradiography. Where the label is a fluorescent label, it may be detected by exciting the fluorophore with the appropriate wavelength of light and detecting the resulting fluorescence. The fluorescence may be detected visually, by means of a photographic film, by the use of electronic detectors such as charge coupled devices (CCDs) or photomultipliers and the like. Similarly, enzyme labels may be detected by providing the appropriate substrates for the enzyme and detecting the resulting reaction product. Finally simple colorimetric labels may be detected simply by observing the color associated with the label.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Epidemiological studies have demonstrated several other, known risk factors for neurological diseases. Of the different genetic markers identified, the most important risk factor to date is apolipoprotein E (Apo E) polymorphism for predicting AD. In autosomal dominant early-onset AD, mutations in 3 additional genes have been identified, the amyloid precursor protein (APP), presenilin 1 (PSEN1), and presenilin 2 (PSEN2) genes (Campion et al., 1999; Finckh et al., 2000).

The presenilin-1 (PSEN1) genotype and a CYP46 polymorphism have also been associated with a higher risk of late-onset sporadic AD (Wragg et al., 1996; Papassotiropoulos et al., 2003).

Accordingly, the present invention also relates to a method for determining whether a subject is at risk of developing a neurological disease, comprising the step of detecting the presence or absence of a nucleic acid variant in the MBL genes in combination with the detection of one or more other risk factors. In a preferred embodiment, the presence or absence of a nucleic acid variant in the MBL genes is detected in combination with the ApoE genotype, with a nucleic acid variant in the APP gene, with a nucleic acid variant in the presenilin 1 gene, with a nucleic acid variant in the presenilin 2 gene and/or with a nucleic acid variant in CYP46.

As already discussed, the presence of nucleic acid variants in the MBL genes of a subject may influence the concentration of MBL in the serum of said subject. Promoter mutations in the MBL2 gene are associated with a decreased production of MBL2. All three exon 1 variants are associated with a significant decrease of the MBL2 level. In addition, these exon 1 variants may have impact on the functionality of MBL2. Therefore based on the detection of the presence or absence of one or more MBL nucleic acid variants, protein variants or MBL functional activity in a subject, it can be determined whether a certain therapeutic agent or treatment might be suitable for preventing the neurological disease the subject is expected (has a risk) to develop or for ameliorating the course of the disease and/or reducing its severity. MBL deficiency can be restored by administration of MBL as a therapeutic. Accordingly, the method of the present invention may also be used in determining whether and which therapeutic agent might be suitable for a patient in order to prevent or treat a neurological disease. As used herein, the term "preventing a disease" means inhibiting or reversing the onset of the disease, inhibiting or reversing the initial signs of the disease, inhibiting the appearance of clinical symptoms of the disease. As used herein, the term "treating a disease" includes substantially inhibiting the disease, substantially slowing or reversing the progression of the disease, substantially ameliorating clinical symptoms of the disease or substantially preventing the appearance of clinical symptoms of the disease.

The method of the present invention, therefore, also relates to the treatment or prevention of a neurological disease in a subject, comprising the following:
(a) detecting the presence or absence of one or more MBL nucleic acid variants in said subject; and
(b) administering to the subject a suitable therapeutic agent, selected based on the nucleic acid variant detected in step (a).

The present invention further relates to the use of MBL for the preparation of a medicament for the treatment or prevention of a neurological disease. In a preferred embodiment, MBL is used for the preparation of a medicament for the treatment or prevention of Alzheimer's disease, Pick's disease, Parkinson's disease, dementia with Lewy bodies, Huntington disease, chromosome 13 dementias, Down's syndrome, cerebrovascular disease, multiple sclerosis, Rasmussen's encephalitis, viral meningitis, NPSLE, amyotrophic lateral sclerosis, Creutzfeldt-Jacob disease, Gerstmann-Straussler-Scheinker disease, transmissible spongiform encephalopathies, ischemic reperfusion damage (e.g. stroke), brain trauma, microbial infection or chronic fatigue syndrome.

Possible treatments include (but are not limited to) the application of MBL to the patient in its native confirmation, in an altered structure or conformation and/or with a different number (size) of oligomers. MBL can be isolated from donor plasma or prepared by recombinant DNA techniques or synthetically. For example, MBL2 can be purified from pooled donor plasma by the procedure developed at Statens Serum Institut (Copenhagen, Denmark) (Valdimarsson et al., 1998). Recombinant DNA techniques have been described by Jensenius et al. (2003) and further by Maniatis (1989) and in WO 96/29605. Classical chemical synthesis is described by Houbenweyl (1974), Atherton and Shepard (1989) and in WO 96/29605.

MBL can be safely administered intravenously in doses sufficient for achieving normal concentrations in the blood. Formulation of the MBL product for intravenous infusion has been described in Valdimarsson et al. (1998). MBL is diluted to 200 µg/ml in 0.15M NaCl containing 1% (w/v) human serum albumin (Valdimarsson et al., 1998). It should be clear, however, that also other formulations can be used for administering the MBL product to the subject. The preferred formulation of therapeutic compositions depends on the intended mode of administration and application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or non-toxic, nontherapeutic, nonimmunogenic stabilizers and the like.

The pharmaceutical compositions can also include large, slowly metabolized macromolecules such as proteins, polysaccharides, polylactic acids, polyglycolic acids and copolymers (such as latex functionalized sepharose, agarose, cellulose, and the like), polymeric amino acids, amino acid copolymers, and lipid aggregates (such as oil droplets or liposomes).

For parenteral administration, the compositions of the invention can be administered as injectable dosages of a solution or suspension of the substance in a physiologically acceptable diluent with a pharmaceutical carrier that can be a sterile liquid such as water, oils, saline, glycerol, or ethanol. Also encapsulation into biodegradable microparticles can be used as a parenteral delivery system (Brayden et al., 2001).

Additionally, auxiliary substances, such as wetting or emulsifying agents, surfactants, pH buffering substances and the like can be present in the therapeutic compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Typically, compositions are prepared as injectables, either as liquid solutions or suspensions. Solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (Langer, 1990; Langer et al, 1997). The pharmaceutical compositions can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides. Such suppositories can be formed from mixtures containing the active ingredient in the range of 0.5% to 10%, preferably 1% to 2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations, or powders and contain 10% to 95% of active ingredient, preferably 25% to 70%.

Topical application can result in transdermal or intradermal delivery. Topical administration can be facilitated by co-administration of the agent with cholera toxin or detoxified derivatives or subunits thereof or other similar bacterial toxins (Glenn et al., 1998). Co-administration can be achieved by using the components as a mixture or as linked molecules obtained by chemical crosslinking or expression as a fusion protein.

Alternatively, transdermal delivery can be achieved using a skin path or using transferosomes (Paul et al., 1995; Cevc et al., 1998).

Further techniques for formulation and administration of drugs can also be found in "Remington's Pharmaceutical Sciences".

Given the clear link between the presence of nucleic acid variants in the MBL genes of a subject and the concentration and functionality of MBL in the serum of said subject, the possibility exists that said subject expected (or at risk) to develop a neurological disease could be treated by one or other forms of "gene therapy". In this way a defective MBL gene could be corrected, repaired and/or replaced resulting in the provision of normal concentrations and/or differently functioning MBL in said subject. Accordingly, in another embodiment, the present invention relates to the use of a nucleic acid containing one or more variants in the MBL gene (variant nucleic acid) for the manufacture of a medicament for the treatment or prevention of a neurological disease. In a preferred embodiment, the variant sequence is comprised within the promoter region, the 5' UR or the exon 1 of the MBL2 gene. In another preferred embodiment, the variant sequence is in at least one of the positions −550, −221, +4, +154, +161 and/or +170 of the MBL2 gene. In another preferred embodiment, the variant sequence encompasses nucleotide T, at position +154 (variant D), nucleotide A at position +161 (variant B) and/or nucleotide A at position +170 (variant C) in the MBL2 gene. In another preferred embodiment, the variant sequence encompasses nucleotide G at position −221 (variant Y) in the MBL2 gene. In a preferred embodiment, MBL gene therapy is used for the preparation of a medicament for the treatment or prevention of Alzheimer's disease, Pick's disease, Parkinson's disease, dementia with Lewy bodies, Huntington disease, chromosome 13 dementias, Down's syndrome, cerebrovascular disease, multiple sclerosis, Rasmussen's encephalitis, viral meningitis, NPSLE, amyotrophic lateral sclerosis, Creutzfeldt-Jacob disease, Gerstmann-Straussler-Scheinker disease, transmissible spongiform encephalopathies, ischemic reperfusion damage (e.g. stroke), brain trauma, microbial infection or chronic fatigue syndrome.

In order to facilitate the introduction of a nucleic acid molecule into cells, a number of different means for gene delivery can be used in association with the nucleic acid molecule. The term "means for gene delivery" is meant to include any technique suitable for delivery of nucleic acid molecules across the blood brain barrier and/or for transmembrane delivery across cell membranes. Non-limiting examples of means for gene delivery are viral vectors (e.g., adeno-associated virus-based vectors, lipids/liposomes, ligands for cell surface receptors, etc). The nucleic acids or a vector containing the same, can be packaged into liposomes. Suitable lipids and related analogs are described by U.S. Pat. No. 5,208,036, 5,264,618, 5,279,833, and 5,283,185. Vectors and nucleic acids can also be adsorbed to or associated with particulate carriers, examples of which include polymethyl methacrylate polymers and polylactides and poly(lactide-co-glycolides) (McGee et al., 1997). Gene therapy vectors or naked nucleic acids can be delivered in vivo by administration to an individual patient, typically by systemic administration (e.g., intravenous, intraperitoneal, nasal, gastric, intradermal, intramuscular, subdermal, or intracranial infusion) or topical application (see e.g., U.S. Pat. No. 5,399,346). The nucleic acid can also be administered using a gene gun (Xiao and Brandsma, 1996). The nucleic acid is precipitated onto the surface of microscopic metal beads. The microprojectiles are accelerated with a shock wave or expanding helium gas, and penetrate tissues to a depth of several cell layers. For example, The Accel™ Gene Delivery Device manufactured by Agacetus, Inc. (Middleton Wis., US) is suitable. Alternatively, naked nucleic acids can pass through skin into the blood stream simply by spotting the nucleic acid onto skin with chemical or mechanical irritation (WO 95/05853). In a further variation, vectors encoding the variant nucleic acid, can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Effective doses of the therapeutic compositions of the present invention vary depending upon many different factors, including means of administration, target site, physiological state of the subject, whether the subject is a human or an animal, other medications administered, and whether treatment is prophylactic or therapeutic. Treatment dosages need to be titrated to optimize safety and efficacy. Examples of effective doses are described in Valdimarsson et al. (1998), Garred et al. (2002) and Validmarsson (2003).

Another aspect of the invention relates to a kit for determining whether a subject is at risk of developing a neurological disease. This kit can be based on the detection of nucleic acid variants in the MBL genes of said subject or it can be based on the measurement of MBL protein variants or MBL functional activity.

The kit may comprise:
 (a) a means for detecting the presence or absence of one or more nucleic acid variants in the MBL genes of said subject, for measuring the concentration of one or more MBL protein variants in said subject and/or for measuring the MBL functional activity in said subject; and
 (b) a means for determining, from the nucleic acid variants, the protein variant concentration and/or the functional activity detected with the means of step (a), whether the subject is at risk of developing a neurological disease.

In a preferred embodiment of the present invention, the kit comprises:
 (a) a means for detecting the presence or absence of one or more nucleic acid variants at positions +154 (C>T), +161 (G>A) and/or +170 (G>A) of the MBL2 genes of said subject; and
 (b) a means for determining, from the nucleic acid variants detected with the means of step (a), whether the subject is at risk of developing a neurological disease, whereby the absence of nucleotide T at position +154 (variant D), nucleotide A at positions +161 (variant B) and nucleotide A at position +170 (variant C) of the MBL2 gene indicates that the subject is at risk of developing a neurological disease such as AD.

In another preferred embodiment of the present invention, the kit comprises:
(a) a means for detecting the MBL haplotype of said subject; and
(b) a means for determining, from the haplotypes detected with the means of step (a), whether the subject is at risk of developing a neurological disease, whereby the absence of the haplotypes HYPD, LYPB and LYQC indicates that the subject is at risk of developing a neurological disease such as AD.

In another preferred embodiment of the present invention, the kit comprises:
(a) a means for detecting the presence or absence of one or more nucleic acid variants at position −221 (G>C) of the MBL2 genes of said subject; and
(b) a means for determining, from the nucleic acid variants detected with the means of step (a), whether the subject is at risk of developing a neurological disease, whereby the presence of nucleotide C at position −221 (variant X) of the MBL2 genes indicates that the subject is at risk of developing a neurological disease such as AD.

In another preferred embodiment of the present invention, the kit comprises:
(a) a means for detecting the MBL haplotype of said subject; and
(b) a means for determining, from the haplotypes detected with the means of step (a), whether the subject is at risk of developing a neurological disease, whereby the presence of the haplotype LXPA indicates that the subject is at risk of developing a neurological disease such as AD.

In another preferred embodiment of the present invention, the kit comprises:
(a) a means for detecting the MBL haplotype of said subject; and
(b) a means for determining, from the haplotypes detected with the means of step (a), whether the subject is at risk of developing a neurological disease, whereby the presence of the haplotype LYPA indicates that the subject is at risk of developing a neurological disease such as MS.

In a specific embodiment the means in step (a) of said kit may comprise:
(i) when appropriate, a means for obtaining a target MBL2 polynucleic acid present in a biological sample and/or obtaining the nucleotide sequence thereof;
(ii) when appropriate, at least one oligonucleotide pair suitable for amplification of a target MBL2 polynucleic acid comprising the nucleic acid sequences at positions −550, −221, +4, +154, +161, and/or +170;
(iii) when appropriate, a means for denaturing nucleic acids;
(iv) when appropriate, at least one oligonucleotide suitable for detection of a target MBL2 polynucleic acid comprising the nucleic acid sequences at positions −550, −221, +4, +154, +161, and/or +170;
(v) when appropriate, an enzyme capable of modifying a double stranded or single stranded nucleic acid molecule;
(vi) when appropriate, a hybridization buffer, or components necessary for producing said buffer;
(vii) when appropriate, a wash solution, or components necessary for producing said solution;
(viii) when appropriate, a means for detecting partially or completely denatured polynucleic acids and/or a means for detecting hybrids formed in the preceding hybridization and/or a means for detecting enzymatic modifications of nucleic acids;
(ix) when appropriate, a means for attaching an oligonucleotide to a known location on a solid support.

The term "hybridization buffer" means a buffer allowing a hybridization reaction between the probes and the polynucleic acids present in the sample, or the amplified products, under the appropriate stringency conditions.

The term "wash solution" means a solution enabling washing of the hybrids formed under the appropriate stringency conditions.

In a more specific embodiment of the kit, the means for detecting the presence or absence of nucleic acid variants in the MBL genes is a line probe assay (LiPA; Stuyver et al., 1996; Stuyver et al., 1997; Van Geyt et al., 1998). In this embodiment, the selected set of probes is immobilized to a membrane strip in a line fashion. An alternative is immobilization in a dot fashion. Said probes may be immobilized individually or as mixtures to the delineated locations. The amplified MBL polynucleic acids can be labelled with biotine, and the hybrid can then, via a biotine-streptavidine coupling, be detected with a non-radioactive colour developing system. Particularly advantageous are other systems in which different nucleic acid variants can be detected simultaneously. In this multiparameter approach, oligonucleotides may be coupled to microspheres or chips. An example of an assay that provides for simultaneous detection includes (but is not limited to) the xMAP™ technology (Luminex 100 IS, Austin, Tex., USA), the PamGene technology (PamGene, 's-Hertogenbosch, The Netherlands) and the Invader® platform (Third Wave Technologies, Inc., Madison, Wisc., US).

A kit based on the detection of MBL protein variants may comprise an antibody that specifically recognizes the MBL protein variant that is detected. A preferred kit for carrying out the method of the invention comprises:
an antibody (primary antibody) which forms an immunological complex with the MBL protein variant to be detected;
a monoclonal antibody (secondary antibody) which specifically recognizes the MBL protein variant to be detected;
a marker either for specific tagging or coupling with said secondary antibody;
appropriate buffer solutions for carrying out the immunological reaction between the primary antibody and the MBL protein variant, between the secondary antibody and the primary antibody-MBL protein variant complex and/or between the bound secondary antibody and the marker;
possibly, for standardization purposes, a purified MBL protein variant.

In a preferred embodiment of the present invention, the kit comprises:
(a) an antibody that specifically recognizes the MBL protein variant with C at amino acid position 52 (variant D), D at amino acid position 54 (variant B) and/or E at amino acid position 57 (variant C); and
(b) a means for determining, from the MBL protein variant concentration measured with the means of step (a), whether the subject is at risk of developing a neurological disease, whereby the absence of the MBL protein variant with C at amino acid position 52 (variant D), D at position 54 (variant B) and E at position 57 (variant C)

indicates that the subject is at risk of developing a neurological disease such as AD.

The means in step (b) of said kit, for determining, from the nucleic acid variants in the MBL gene, the MBL protein variant concentration and/or the MBL functional activity detected with the means of step (a), whether the subject is at risk of developing a neurological disease include a table, a chart, or similar, generally referred to as "a predisposition risk algorithm", taking into account the MBL nucleic acid variant(s) or haplotype(s), the MBL protein variant concentration and/or the MBL functional activity to determine the risk for developing a neurological disease. It may indicate the MBL nucleic acid variant or haplotype, the MBL protein variant concentration and/or the MBL functional activity that confer a risk for developing a neurological disease and/or it may indicate the MBL nucleic acid variant or haplotype, the MBL protein variant concentration and/or the MBL functional activity that confer protection for not developing a neurological disease.

The determination of the risk can be performed manually or with the use of a computer. Accordingly, the present invention also provides a method for determining whether a subject is at risk of developing a neurological disease making use of a computer. In this method, information, for example, on the MBL nucleic acid variant or haplotype, the MBL protein variant concentration and/or the MBL functional activity that confer a risk for developing a neurological disease and the MBL nucleic acid variant or haplotype, the MBL protein variant concentration and/or the MBL functional activity that confer protection for not developing a neurological disease is introduced into a computer by an operator. In one embodiment, this information is stored on a computer readable carrier. "Computer readable carriers" or "computer readable media" include all carriers and media accessible and readable with a computer. Said carriers and media include magnetic tapes, floppy disks, hard disks, ZIP disks, CD-ROMs, electrical or electronical memories such as RAM and ROM and hybrid magnetic/optical storage media. After the correlation, the results of the comparison or assessment can be displayed on the computer on a display device such as, for example, a computer monitor or outputted on for example, a printer. T he kit of the present invention may include, in additions to the means of steps (a), a means for detection other risk factors for developing a neurological disease. In a preferred embodiment, the kit additionally includes a means for detecting the Apo E genotype, a means for detecting a nucleic acid variant in the APP gene, a means for detecting a nucleic acid variant in the presenilin 1 gene, a means for detecting a nucleic acid variant in the presenilin 2 gene and/or a means for detecting a nucleic acid variant in CYP46.

Accordingly, the present invention relates to a kit comprising:
  (a) a means for detecting the presence or absence of one or more nucleic acid variants in the MBL genes of said subject, for measuring the concentration of one or more MBL protein variants in said subject and/or for measuring the MBL functional activity in said subject; and
  (b) a means for detecting the presence or absence of a nucleic acid variant in at least one of the following: the ApoE gene, the APP gene, the presenilin 1 gene, the presenilin 2 gene, CYP46.

Throughout this specification and the claims which follow, unless the context requires otherwise, the word "comprise", and variations such as "comprises" and "comprising", will be understood to imply the inclusion of a stated integer or step or group of stated integers or steps but not to the exclusion of any other integer or step or group of integers or steps.

EXAMPLES

Example 1

Detection of Nucleic Acid Variants in the MBL2 Alleles from Alzheimer's Disease Patients and from Control Subjects Patients Samples A study was carried out based on blood samples archived at the Sahlgren's University Hospital, Goteborg, Sweden, including 174 AD patients from Caucasian origin. All patients with AD satisfied the NINCDS-ADRDA criteria (McKhann et al., 1984). The control group (C) consisted of 124 individuals without histories, symptoms, or signs of psychiatric or neurological disease.

The Ethics Committees of the University of Göteborg and Umea, Sweden, approved the study. All patients (or their nearest relatives) and controls gave informed consent to participate in the study, which was conducted according to the provisions of the Declaration of Helsinki.

Detection of Nucleic Acid Polymorphisms

To determine the presence or absence of nucleic acid variants in the MBL2 alleles, a part of the exon 1 and promoter sequences of MBL2 was amplified using biotinylated oligonucleotides. The polymorphisms were detected by use of a reverse hybridization method (Line Probe Assay) with 12 probes designed to recognize the polymorphisms at positions −550 (G>C), −221 (G>C), +4 (C>T), +154 (C>T), +161 (G>A) and +170 (G>A) of MBL2. After stringent washing at 56° C., hybridized probes were incubated with a streptavidine-alkaline phosphatase conjugate. The presence of a hybridized probe was revealed using NBIT/BCIP color development. Details on the reverse hybridization are described in Stuyver et al. (1996), Stuyver et al. (1997) and Van Geyt et al. (1998).

Statistical Analysis

174 AD-diagnosed (2n=348 haplotypes) and 124 C-diagnosed subjects (2n=248 haplotypes) were genotyped for MBL2 (2n=596 haplotypes). Data (all haplotypes) were modeled as 2XC-tables where rows indicate diagnosis (1=AD and 2=C) and columns haplotype. Association between HAPLO and diagnosis (AD vs C) was investigated with Fisher Exact tests. For large tables, P-values were obtained using Monte Carlo simulations. For 2×2-tables (Table 1), the strength of association was reported as odds ratios (OR) (with 95% lower (LCL) and upper (UCL) confidence limit), indicating the factor by which the risk of developing AD is increased. All reported tests are two-tailed. A test was concluded to be significant if the P-value was less than 0.05 after correction for multiple testing (Bonferroni procedure). Analyses were performed using PROC FREQ in SAS (version 8.02, SAS Institute Inc. N.C., USA).

Frequencies of MBL2 Haplotypes in AD and Control Subjects

The frequencies of the MBL2 haplotypes in the AD patients and in the control subjects are indicated in Table 2. The promoter variant X (haplotype LXPA) is more frequently present in the AD group compared to the control group. The odds ratios in Tables 1 and 2 clearly show that promoter variant X (haplotypes LXPA) has a significantly higher risk for developing AD. Upon examination of the variant alleles, significant differences were also observed for the B and C variants, which are less prevalent in the AD group. Tables 1 and 2 show that the haplotypes with these variants (LYPB and LYQC) indeed have a lower risk of developing AD.

Example 2

Determination of the MBL2 Haplotypes in Alzheimer's Disease Patients and Control Subjects Patients Samples A study was carried out including 523 AD patients and 285 control subjects. Swedish samples from Pitea (n=174, AD, blood samples) were collected as part of a longitudinal geriatric population study in Pitea, Sweden. All clinically diagnosed AD patients underwent a thorough investigation, which included a medical history, physical, neurological, and psychiatric examination, screening laboratory tests, ECG, X-ray of the chest, EEG, and computerized tomography (CT) of the brain. Clinical AD diagnosis were made according the the NINCDS-ADRDA criteria.

Samples from MAS (n=273, AD, blood samples), NOMAS (n=56, control, blood samples), Gbg (n=72, control, blood samples), Linköping (n=14, control, blood samples), Mö (n=23, control, brain samples), Ne (n=54, control, brain samples) were collected from a prospective longitudinal study of patients with dementia (the Mölndal prospective dementia study). Clinical diagnosis was made according to the NINCDS-ADRDA criteria. The neuropathological scoring system was applied to the autopsy controls, using an index of senile plaques (SP) and neurofibrillary tangles (NFT) density on a 12-graded scale (Alafuzoff et al., 1987). At autopsy, brains were weighed, and infarcts and lacunas were noted on circumspect gross examination. Two areas of the right hemisphere, the frontal lobe and the anterior part of the hippocampal formation, were fixed in 10% buffered neutral formalin for 4-6 weeks, and then embedded in paraffim blocks. Sections were stained by the Bielschowsky silver impregnation technique. The absolute number of SPs and NFTs was assessed in five randomly selected fields at magnification ×125 and a mean count of SPs and NFTs was obtained, averaged over both brain regions.

The healthy controls were volunteers without history, symptoms, or signs of psychiatric or neurological disease, malignant disease, or systemic disorders. Cognitive status was examined using MMSE, and individuals with scores below 28 were not included as controls.

The AD samples from INSERM (n=76, brain) were part of a prospective longitudinal study of patients with dementia (Delacourte et al., 1999), while the controls (n=66, blood) were matched for age and sex and underwent a thorough clinical examination as described for the Swedish controls.

The Ethics Committees of the different centers that collected the blood samples, approved the study. All patients (or their nearest relatives) and controls gave informed consent to participate in the study, which was conducted according to the provisions of the Declaration of Helsinki.

Detection of Nucleic Acid Polymorphisms

To determine the presence or absence of nucleic acid variants in the MBL2 alleles, a part of the exon 1 and promoter sequences of MBL2 was amplified using biotinylated oligonucleotides. The polymorphisms were detected by use of a reverse hybridization method (Line Probe Assay) with 12 probes designed to recognize the polymorphisms at positions −550 (G>C), −221 (G>C), +4 (C>T), +154 (C>T), +161 (G>A) and +170 (G>A) of MBL2. After stringent washing at 56° C., hybridized probes were incubated with a streptavidine-alkaline phosphatase conjugate. The presence of a hybridized probe was revealed using NBIT/BCIP color development. Details on the reverse hybridization are described in Stuyver et al. (1996), Stuyver et al. (1997) and Van Geyt et al. (1998).

Statistical Analysis

A logistic regression approach (Zhao et al. 2003) was used to test whether the MBL2-haplotype predicts the risk of developing AD. In other words, this approach tests whether the presence of a certain haplotype increases the chance of developing AD while the presence of certain other haplotypes protects a patient from developing AD. The strength of association is reported as an odds ratio (OR) with 95% lower (LCL) and upper (UCL) confidence limits. For a gene (the MBL2-gene) modeled as a set of dummy variables (here, one for each haplotype), it should be interpreted as compared with a reference haplotype (Zhao et al. 2003). Accordingly, the following models were tested:

Model 1: LXPA versus the pooled other haplotypes;

Model 2: Pooled haplotypes HYPD, LYPB and LYQC versus the pooled other haplotypes;

Model 3: LXPA versus the pooled haplotypes HYPD, LYPB and LYQC versus the pooled haplotypes HYPA, LYPA and LYQA.

All analyses are done with SAS version 8.2. Logistic regression analysis is conducted using PROC LOGISTIC with binomial error structure and logit link function. All reported tests are two-tailed. A test is considered significant if $P<0.05$.

Frequencies of MBL2 Haplotypes in AD and Control Subjects

The frequencies of the MBL2 haplotypes and combined MBL2 haplotypes in the AD patients and in the control subjects are shown in Tables 3 and 4 respectively. The probability of developing AD was compared between i) LXPA, ii) HYPD, LYPB and LYQC, and iii) HYPA, LYPA and LYQA (see statistical models above). Results of the logistic regression analyses are presented in Table 5. AIC-values are quite similar suggesting that the models are equally acceptable. For none of the models there was a significant effect of sex on disease incidence (all P>0.78). In all models there was a significant effect of subpopulation (P<0.0001): there were more patients with AD in the center group MAS than in the center groups Pitea and INSERM. In all models, age was positively related with AD-incidence (P<0.0001). In all models the presence of the ApoE4 allele significantly increased the AD-incidence (P<0.0001). For none of the models there was a significant interaction between the ApoE genotype and MBL2-(pooled) haplotype (all P>0.45). Model 1 shows that the MBL2-haplotype LXPA increased AD-incidence as compared with other pooled MBL2-haplotypes (P<0.013, OR >1). Model 2 shows that pooled MBL2-haplotypes HYPD, LYPB and LYQC decreased AD-incidence as compared with other pooled MBL2-haplotypes (P<0.006, OR <1). When MBL2-haplotype LXPA and the pooled MBL2-haplotypes HYPD, LYPB and LYQC are tested in one model (Model 3), it appears that pooled MBL2-haplotypes HYPD, LYPB and LYQC decreased AD-incidence while MBL2-haplotype LXPA increased AD-incidence compared with pooled MBL2-haplotypes HYPA, LYPA and LYQA, but the latter not significantly so (P=0.0657). It can therefore be concluded that the presence of the LXPA haplotype increases the risk of developing AD, whereas the presence of the haplotypes HYPD, LYPB and LYQC has a protective effect on the development of AD.

Example 3

Determination of the MBL2 Haplotypes in Multiple Sclerosis Patients and Control Subjects Patients Samples A study was carried out based on blood samples from 61 patients with proven multiple sclerosis. The control group (C) consisted of 172 healthy individuals. From each blood sample, informed consent to participate in the study is available Detection of Nucleic acid Polymorphisms To determine the MBL2 genotypes, the relevant coding sequences of the MBL2 gene were amplified using biotinylated oligonucleotides. The polymorphisms were detected by use of a reverse hybridization method (Line Probe Assay) with 12 probes designed to recognize the polymorphisms at positions −550 (G>C), −221 (G>C), +4 (C>T), +154 (C>T), +161 (G>A) and +170 (G>A) of MBL2. After stringent washing at 56° C., hybridized probes were incubated with a streptavidine-alkaline phosphatase conjugate. The presence of a hybridized probe was revealed using NBIT/BCIP color development. Details on the reverse hybridization are described in Stuyver et al. (1996), Stuyver et al. (1997) and Van Geyt et al. (1998).

Statistical Analysis 61 patients with MS and 172 C-diagnosed subjects were genotyped for the 6 SNPs in the MBL2 gene. Associations were tested using multiple logistic regression. The strength of association was reported as odds ratios (OR), indicating the factor by which the risk of developing multiple sclerosis is increased or decreased. The 95% confidence interval (95% CI) is the interval computed from the sample data which, were the study repeated multiple times, would contain the true effect 95% of the time.

Results

Logistic regression analysis (backward elimination) revealed that there was a significant association between MS-susceptibility and MBL2-haplotype: carrying LYPA increased the probability (Wald chisquare=4.1385, df=1, P=0.0419) to belong to the diseased group (OR=2.297, 95% LCL =1.031; 95% UCL=5.117).

TABLES

TABLE 1

2 × 2 table indicating all possible pairwise haplotype combinations and their Odds ratio.

| Haplotype comparison | Exact P | Estimate | Exact 95% LCL | Exact 95% UCL |
|---|---|---|---|---|
| | | | Odds ratio | |
| HYPA vs HYPD | 0.38133 | 0.71570 | 0.32291 | 1.53460 |
| HYPA vs LXPA | 0.04426 | 0.60563 | 0.36717 | 0.99519 |
| HYPA vs LYPA | 0.56556 | 1.29909 | 0.57082 | 2.93889 |
| HYPA vs LYPB | 0.10937 | 1.61033 | 0.86989 | 2.98521 |
| HYPA vs LYQA | 1.00000 | 1.02589 | 0.62786 | 1.67401 |
| HYPA vs LYQC | 0.00520 | 4.83099 | 1.42643 | 20.83878 |
| HYPD vs LXPA | 0.70349 | 0.84621 | 0.38384 | 1.92843 |
| HYPD vs LYPA | 0.24085 | 1.81513 | 0.64085 | 5.15590 |
| HYPD vs LYPB | 0.07129 | 2.25000 | 0.93382 | 5.51057 |
| HYPD vs LYQA | 0.36641 | 1.43340 | 0.65274 | 3.24344 |
| HYPD vs LYQC | 0.00394 | 6.75000 | 1.64617 | 32.47216 |
| LXPA vs LYPA | 0.06548 | 2.14501 | 0.91626 | 4.97155 |
| LXPA vs LYPB | 0.00190 | 2.65891 | 1.38748 | 5.09148 |
| LXPA vs LYQA | 0.04310 | 1.69390 | 0.99652 | 2.88315 |
| LXPA vs LYQC | 0.00015 | 7.97674 | 2.29739 | 34.72304 |
| LYPA vs LYPB | 0.67199 | 1.23958 | 0.49255 | 3.12266 |
| LYPA vs LYQA | 0.56137 | 0.78970 | 0.34170 | 1.83555 |
| LYPA vs LYQC | 0.07293 | 3.71875 | 0.88553 | 18.39616 |
| LYPB vs LYQA | 0.17010 | 0.63707 | 0.33448 | 1.21201 |
| LYPB vs LYQC | 0.10332 | 3.00000 | 0.81352 | 13.70217 |
| LYQA vs LYQC | 0.00580 | 4.70909 | 1.36577 | 20.52358 |

TABLE 2

Frequencies of MBL haplotypes in AD patients and in healthy controls.

| MBL2 haplotype | AD (2n = 348) | Control (2n = 248) | P value | Odds ratio |
|---|---|---|---|---|
| HYPA | 28% (98) | 29% (71) | | |
| HYPD | 8% (27) | 6% (14) | | |
| LYPA | 5% (17) | 6% (16) | | |
| LYQA | 21% (74) | 22% (55) | | |
| LXPA | 28% (98) | 17% (43) | 0.0024 | 1.87 (95% CI 1.23-2.87) |
| LYPB | 8% (30) | 14% (35) | | |
| LYQC | 1.1% (4) | 6% (14) | | |
| LY*O | 10% (34) | 20% (49) | 0.0007 | 0.44 (95% CI 0.27-0.72) |

( ): number of cases; CI: confidence interval.

TABLE 3

Frequency of the different haplotypes in AD patients (AD) and in control subjects (C)

| MBL2 haplotype | AD n | AD % | C n | C % | total n |
|---|---|---|---|---|---|
| HYPA | 322 | 64.53 | 177 | 35.47 | 499 |
| HYPD | 83 | 61.48 | 52 | 38.52 | 135 |
| LXPA | 231 | 68.14 | 108 | 31.86 | 339 |
| LYPA | 46 | 53.49 | 40 | 46.51 | 86 |
| LYPB | 128 | 60.95 | 82 | 39.05 | 210 |
| LYQA | 211 | 68.51 | 97 | 31.49 | 308 |
| LYQC | 25 | 64.10 | 14 | 35.90 | 39 |
| | | | | | 1616 |

TABLE 4

Frequency of the combined haplotypes in AD patients (AD) and in control subjects (C).

| Combined MBL2 haplotype | AD n | AD % | C n | C % | total n |
|---|---|---|---|---|---|
| HYPA-HYPA | 48 | 58.54 | 34 | 41.46 | 82 |
| HYPA-HYPD | 24 | 61.54 | 15 | 38.46 | 39 |
| HYPA-LXPA | 79 | 76.70 | 24 | 23.30 | 103 |
| HYPA-LYPA | 14 | 66.67 | 7 | 33.33 | 21 |
| HYPA-LYPB | 44 | 64.71 | 24 | 35.29 | 68 |
| HYPA-LYQA | 58 | 63.04 | 34 | 36.96 | 92 |
| HYPA-LYQC | 7 | 58.33 | 5 | 41.67 | 12 |
| HYPD-HYPD | 2 | 66.67 | 1 | 33.33 | 3 |
| HYPD-LXPA | 19 | 59.38 | 13 | 40.63 | 32 |

TABLE 4-continued

Frequency of the combined haplotypes in AD patients (AD) and in control subjects (C).

| Combined MBL2 haplotype | AD n | AD % | C n | C % | total n |
|---|---|---|---|---|---|
| HYPD-LYPA | 2 | 28.57 | 5 | 71.43 | 7 |
| HYPD-LYPB | 12 | 57.14 | 9 | 42.86 | 21 |
| HYPD-LYQA | 19 | 79.17 | 5 | 20.83 | 24 |
| HYPD-LYQC | 3 | 50.00 | 3 | 50.00 | 6 |
| LXPA-LXPA | 25 | 73.53 | 9 | 26.47 | 34 |
| LXPA-LYPA | 12 | 57.14 | 9 | 42.86 | 21 |
| LXPA-LYPB | 29 | 64.44 | 16 | 35.56 | 45 |
| LXPA-LYQA | 37 | 58.73 | 26 | 41.27 | 63 |
| LXPA-LYQC | 5 | 71.43 | 2 | 28.57 | 7 |
| LYPA-LYPA | 3 | 60.00 | 2 | 40.00 | 5 |
| LYPA-LYPB | 3 | 25.00 | 9 | 75.00 | 12 |
| LYPA-LYQA | 9 | 60.00 | 6 | 40.00 | 15 |
| LYPB-LYPB | 4 | 50.00 | 4 | 50.00 | 8 |
| LYPB-LYQA | 30 | 68.18 | 14 | 31.82 | 44 |
| LYPB-LYQC | 2 | 50.00 | 2 | 50.00 | 4 |
| LYQA-LYQA | 26 | 83.87 | 5 | 16.13 | 31 |
| LYQA-LYQC | 6 | 75.00 | 2 | 25.00 | 8 |
| LYQC-LYQC | 1 | 100.00 | 0 | 0.00 | 1 |
|  | 523 |  | 285 |  | 808 |

Note that genotype LYPA-LYQC does not occur in this sample. This should not have a strong impact on results presented further in the description.

TABLE 5

Results of logistic regression analyses for the three statistical models.

| Variable | df | Chisq | P | Effect | OR | LCL | UCL |
|---|---|---|---|---|---|---|---|
| Model 1: AIC = 818.92 | | | | | | | |
| Centers[a] | 2 | 51.85 | 0.0000 | inserm vs pitea | 1.12 | 0.71 | 1.76 |
|  |  |  |  | mas vs pitea | 4.04 | 2.73 | 5.98 |
| Age | 1 | 26.47 | 0.0000 |  | 1.06 | 1.03 | 1.08 |
| ApoE4 | 1 | 80.64 | 0.0000 |  | 3.89 | 2.89 | 5.23 |
| LXPA | 1 | 6.20 | 0.0127 |  | 1.47 | 1.09 | 1.99 |
| HYPD, LYPB, LYQC, HYPA, LYPA, LYQA | 0 | | | | | | |
| Model 2: AIC = 817.64 | | | | | | | |
| Centers[a] | 2 | 52.10 | 0.0000 | inserm vs pitea | 1.08 | 0.69 | 1.70 |
|  |  |  |  | mas vs pitea | 4.04 | 2.73 | 5.99 |
| Age | 1 | 28.17 | 0.0000 |  | 1.06 | 1.04 | 1.08 |
| ApoE4 | 1 | 80.64 | 0.0000 |  | 3.88 | 2.89 | 5.22 |
| HYPD, LYPB, LYQC | 1 | 7.57 | 0.0059 |  | 0.67 | 0.50 | 0.89 |
| LXPA, HYPA, LYPA, LYQA | 0 | | | | | | |
| Model 3: AIC = 816.20 | | | | | | | |
| Center[a] | 2 | 53.63 | 0.0000 | inserm vs pitea | 1.10 | 0.70 | 1.73 |
|  |  |  |  | mas vs pitea | 4.18 | 2.81 | 6.22 |
| Age | 1 | 27.08 | 0.0000 |  | 1.06 | 1.03 | 1.08 |
| ApoE4 | 1 | 81.10 | 0.0000 |  | 3.92 | 2.91 | 5.28 |
| LXPA | 1 | 3.39 | 0.0657 |  | 1.34 | 0.98 | 1.84 |
| HYPD, LYPB, LYQC | 1 | 4.69 | 0.0304 |  | 0.72 | 0.53 | 0.97 |
| HYPA, LYPA, LYQA | 0 | | | | | | |

[a]The 8 centers where blood samples were collected were grouped into 3 groups:
Inserm: including INSERM
Mas: including MAS and NOMAS
Pitea: including Götegorg, Linköping, Mö, Ne and Pitea

REFERENCES

Alafuzoff I., Iqbal K., Friden H., Adolfsson R., Winblad B. (1987) Histopathological criteria for progressive dementia disorders: clinical-pathological correlation and classification by multivariate data analysis. Acta Neuropathol. (Berl) 74: 209-225.

Alloul K., Sauriol L., Kennedy W., Laurier C., Tessier G., Novosel S. et al. (1998) Alzheimer's disease: a review of the disease, its epidemiology and economic impact. Arch. Gerontol. Geriatr. 27: 189-221.

Armstrong M., Daly A. K., Cholerton S., Bateman D. N., Idle J. R. (1992) Mutant debrisoquine hydroxylation genes in Parkinson's disease. Lancet 339: 1017-1017.

Artiga M. J., Bullido M. J., Sastre I, Recuero M., Garcia M. A., Aldudo J., Vazquez J., Valdivieso F. (1998) Allelic polymorphisms in the transcriptional regulatory region of apolipoprotein E gene. FEBS Lett. 421: 105-108.

Atherton, Shepard. (1989) Solid phase peptide synthesis. Solid phase peptide synthesis. IRL Press, Oxford.

Boldt A. B., Petz-Erler M. L. (2002) A new strategy for mannose-binding lectin gene haplotyping. Hum. Mutat. 19: 296-306.

Brayden D. J., Templeton L., McClean S., Barbour R., Huang J., Nguyen M., Ahem D., Motter R., Johnson-Wood K., Vasquez N., Schenk D., Seubert P. (2001) Encapsulation in biodegradable microparticles enhances serum antibody response to parenterally-delivered β-amyloid in mice. Vaccine 19: 4185-4193.

Campion D., Dumanchin C., Hannequin D., Dubois B., Belliard S., Puel M., Thomas-Anterion C., Michon A., Martin C., Charbonnier F., Raux G., Camuzat A., Penet C., Mesnage V., Martinez M., Clerget-Darpoux F., Brice A., Frebourg T. (1999) Early-onset autosomal dominant Alzheimer disease: prevalence, genetic heterogeneity, and mutation spectrum. Am. J. Hum. Genet. 65: 664-670.

Celis J. E., Gromov P., Ostergaard M., Madsen P., Honore B., Dejgaard K., Olsen E., Vorum H., Kristensen D. B., Gromova I., Haunso A., Van Damme J., Puype M., Vandekerckhove J., Rasmussen H. H. (1996) Human 2-D PAGE databases for proteome analysis in health and disease: http://biobase.dk/cgi-bin/celis. FEBS Lett. 398: 129-134.

Cevc G., Gebauer D., Stieber J., Schatzlein A., Blume G. (1998) Ultraflexible vesicles, Transfersomes, have an extremely low pore penetration resistance and transport therapeutic amounts of insulin across the intact mammalian skin. Biochim Biophys Acta 1368: 201-215.

Christiansen O. B., Kilpatrick D. C., Souter V., Varming K., Thiel S., Jensenius J. C. (1999) Mannan-binding lectin deficiency is associated with unexplained recurrent miscarriage. Scand J Immunol. 49: 193-196.

Corder E. H., Saunders A. M., Strittmatter W. J., Schmechel D. E., Gaskell P. C., Small G. W., Roses A. D., Haines J. L., Pericak-Vance M. A. (1993) Gene dose of apolipoprotein E type 4 allele and the risk of Alzheimer's disease in late onset families. Science 261: 921-923.

Costa P., Checkoway H., Levy D., Smith-Weller T., Franklin G. M., Swanson P. D., Costa L. G. (1997) Association of a polymorphism in intron 13 of the monoamine oxidase B gene with Parkinson disease. Am. J. Med. Genet. 74:154-156.

Croake J. W., Pursley M., Hardin J. G., Michalski J. P. (1998) Systemic lupus erythromatosus and dementia. Psychol. Rep. 83: 1038.

Davidsson P., Westman A., Puchades M., Nilsson C. L., Blennow K. (1999) Characterization of Proteins from Human Cerebrospinal Fluid by a Combination of Preparative Two-Dimensional Liquid-Phase Electrophoresis and Matrix-Assisted Laser Desorption/Ionization Time-of-Flight Mass Spectrometry. Anal. Chem. 71: 642-647.

Delacourte A., David J. P., Sergeant N., Buee L., Wattez A., Vermersch P., Ghozali F., Fallet-Bianco C., Pasquier F., Lebert F., Petit H., Di Menza C. (1999) The biochemical pathway of neurofibrillary degeneration in aging and Alzheimer's disease. Neurology 52: 1158-1165.

den Dunnen J. T., Antonarakis S. E. (2000) Mutation nomenclature extensions and suggestions to describe complex mutations: A discussion. Hum. Mutat. 15: 7-12.

Feinglass E. J., Arnett F. C., Dorsch C. A., Zizic T. M., Stevens M. B. (1989) Neuropsychiatric manifestations of systemic lupus erythomatosus: diagnosis, clinical spectrum, and relationship to other features of the disease. Medicine (Baltimore) 68: 1034.

Finckh U., Muller-Thomsen T., Mann U., Eggers C., Marksteiner J., Meins W., Binetti G., Alberici A., Hock C., Nitsch R. M., Gal A. (2000) High prevalence of pathogenic mutations in patients with early-onset dementia detected by sequence analyses of four different genes. Am. J. Hum. Genet. 66: 110-117.

Garred P., Pressler T., Lanng S., Madsen H. O., Moser C., Laursen I., Balstrup F., Koch C., Koch C. (2002) Mannose-binding lectin (MBL) therapy in an MBL-deficient patient with severe cystic fibrosis lung disease. Pediatr. Pulmonol. 33: 201-207.

Garred P., Larsen F., Madsen H. O., Koch C. (2003) Mannose-binding lectin deficiency-revisited. Review. Mol. Immunol. 40: 73-84.

Ghindilis A. L., Pavlov A. R., Atanassov P. B. (eds.) (2002) Immunoassay Methods and Protocols. Humana Press, Totowa, N.J., US.

Glenn G. M., Rao M., Matyas G. R., Alving C. R. (1998) Skin immunization made possible by cholera toxin. Nature 391: 851.

Gut I. G. (2001) Automation in genotyping of single nucleotide polymorphisms. Hum. Mutat. 17: 475492.

Hanly J. G., Liang M. H. (1997) Cognitive disorders in systemic lupus erythematosus. Epidemiologic and clinical issues. Review. Ann. N. Y. Acad. Sci. 823: 60-68.

Hansen S., Holmskov U. (1998) Structural aspects of collectins and receptors for collectins. Immunobiology 199: 165-189.

Higgins G. A., Large C. H., Rupniak H. T., Barnes J. C. (1997) Apolipoprotein E and Alzheimer's disease: a review of recent studies. Review. Pharmacol. Biochem. Behav. 56: 675-85.

Hoda F., Nicholl D., Bennett P., Arranz M., Aitchison K. J., al-Chalabi A., Kunugi H., Vallada H., Leigh P. N., Chaudhuri K. R., Collier D. A. (1996) No association between Parkinson's disease and low-activity alleles of catechol β-methyltransferase. Biochem. Biophys. Res. Commun. 228: 780-784.

Hotamisligil G. S., Girnen A. S., Fink J. S., Tivol E., Shalish C., Trofatter J., Baenziger J., Diamond S., Markham C., Sullivan J., et al. (1994) Hereditary variations in monoamine oxidase as a risk factor for Parkinson's disease. Mov. Disord. 9: 305-310.

Houbenweyl (1974) Methode der organischen chemie, Vol. 15, I & II. Ed. Wunch E. Thieme, Stuttgart. IRL Press, Oxford.

IFCC. (1987) Approved recommendation on the theory of reference values. Part. 5. Statistical treatment of collected refereece values. Determination of reference limits. J. Clin. Chem. Clin. Biochem. 25: 645-656.

Jensenius J. C., Jensen P. H., McGuire K., Larsen J. L., Thiel S. (2003) Recombinant mannan-binding lectin (MBL) for therapy. Biochem. Soc. Trans.31 (Pt 4):763-767.

Katzmann R., Fox P. J. (1999) The world-wide impact of dementia. Projections of prevalence and costs. In: Mayeux R., Christen Y. (eds.) Epidemiology of Alzheimer's disease: From gene to prevention. Research and perspectives in Alzheimer's disease. Berlin: Springer-Verlag, pp. 1-17.

Kilpatrick D. C. (2002a) Mannan-binding lectin: clinical significance and applications. Biochimica et Biophysica Acta 1572: 401-413.

Kilpatrick D. C. (2002b) Mannan-binding lectin and its role in innate immunity. Transfusion Medicine 12: 335-351.

Klose J., Kobalz U. (1995) Two-dimensional electrophoresis of proteins: an updated protocol and implications for a functional analysis of the genome. Electrophoresis 16: 1034-1059.

Kuhlman M., Joiner K., Ezekowitz R. A. (1989) The human mannose-binding protein functions as an opsonin. J. Exp. Med. 169: 1733-1745.

Kurth J. H., Kurth M. C., Poduslo S. E., Schwankhaus J. D. (1993) Association of a monoamine oxidase B allele with Parkinson's disease. Ann. Neurol. 33: 368-372.

Lambert J. C., Berr C., Pasquier F., Delacourte A., Frigard B., Cottel D., Perez-Tur J., Mouroux V., Mohr M., Cecyre D., Galasko D., Lendon C., Poirier J., Hardy J., Mann D., Amouyel P., Chartier-Harlin M.C. (1998a) Pronounced impact of Th1/E47cs mutation compared with −491 AT mutation on neural APOE gene expression and risk of developing Alzheimer's disease. Hum. Mol. Genet. 7: 1511-1516.

Lambert J. C., Pasquier F., Cottel D., Frigard B., Amouyel P., Chartier-Harlin M. C. (1998b) A new polymorphism in the APOE promoter associated with risk of developing Alzheimer's disease. Hum. Mol. Genet. 7: 533-540.

Langer R. (1990) New methods of drug delivery. 249: 1527-1533.

Langer R., Cleland J. L., Hanes J. (1997) New advances in microsphere-based single-dose vaccines. Adv. Drug Deliv. Rev. 28: 97-119.

Lanzrein A. S., Jobst K. A., Thiel S., Jensenius J. C., Sim R. B., Perry V. H., Sim E. (1998) Mannan-binding lectin in human serum, cerebrospinal fluid and brain tissue and its role in Alzheimer's disease. Neuroreport 9: 1491-1495.

Launer L. J., Andersen K., Dewey M. E., Letenneur L., Ott A., Amaducci L. A., Brayne C., Copeland J. R., Dartigues J. F., Kragh-Sorensen P., Lobo A., Martinez-Lage J. M., Stijnen T., Hofman A. (1999) Rates and risk factors for dementia and Alzheimer's disease: results from EURODEM pooled analyses. EURODEM Incidence Research Group and Work Groups. European Studies of Dementia. Neurology 52: 78-84.

Le Couteur D. G., Leighton P. W., McCann S. J., Pond S. (1997) Association of a polymorphism in the dopamine-transporter gene with Parkinson's disease. Mov. Disord. 12: 760-763.

Lwin A., Orvisky E., Goker-Alpan O., LaMarca M. E., Sidransky E. (2004) Glucocerebrosidase mutations in subjects with parkinsonism. Mol. Genet. Metab. 81: 70-73.

Madsen H. O., Garred P., Kurtzhals J. A., Lamm L. U., Ryder L. P., Thiel S., Svejgaard A. (1994) A new frequent allele is the missing link in the structural polymorphism of the human mannan-binding protein. Immunogenetics 40: 37-44.

Madsen H. O., Garred P., Thiel S., Kurtzhals J. A., Lamm L. U., Ryder L. P., Svejgaard A. (1995) Interplay between promoter and structural gene variants control basal serum level of mannan-binding protein. J. Immunol. 155: 3013-3020.

Manitatis (1989) Molecular Cloning: A Laboratory Manual, $2^{nd}$ Edition, Cold Spring Harbour Laboratory Press.

McCune W. J., Golbus J. (1988) Neuropsychiatric lupus. Review. Rheum. Dis. Clin. North. Am. 14: 149-167.

McGee J. P., Singh M., Li X. M., Qiu H., O'Hagan D. T. (1997) The encapsulation of a model protein in poly (D, L lactide-co-glycolide) microparticles of various sizes: an evaluation of process reproducibility. J. Microencapsul. 14: 197-210.

McKhann G., Drachman D. A., Folstein M. F., Katzman R., Price D. L., Stadlan E. (1984) Clinical diagnosis of Alzheimer's disease: report of the NINCDS-ADRDA Work Group under the auspices of the Department of Health and Human Services Task Force on Alzheimer's disease. Neurology 34: 939-944.

Miller M. E., Seals J., Kaye R., Levitsky L. C. (1968) A familial plasma associated defect of phagocytosis. Lancet 2: 60-63.

Minchinton R. M., Dean M. M, Clark T. R., Heatley S., Mullighan C. G. (2002) Analysis of the relationship between mannose-binding lectin (MBL) genotype, MBL levels and function in an Australian blood donor population. Scand. J. Immunol. 56: 630-641.

Monroe et al. (1986) Amer. Clin. Prod. Rev. 5: 34-41

Mui S., Briggs M., Chung H., Wallace R. B., Gomez-Isla T., Rebeck G. W., Hyman B. T. (1996) A newly identified polymorphism in the apolipoprotein E enhancer gene region is associated with Alzheimer's disease and strongly with the epsilon 4 allele. Neurology 47: 196-201.

Nanko S., Ueki A., Hattori M., Dai X. Y., Sasaki T., Fukuda R., Ikeda K., Kazamatsuri H. (1994) No allelic association between Parkinson's disease and dopamine D2, D3, and D4 receptor gene polymorphisms. Am. J. Med. Genet. 154: 361-364.

Nanko S., Ueki A., Hattori M. (1996) No association between Parkinson's disease and monoamine oxidase A and B gene polymorphisms. Neurosci. Lett. 204: 125-127.

O'Farrell P. H. (1975) High resolution two-dimensional electrophoresis of proteins. J Biol. Chem. 250:40074021.

Papassotiropoulos A., Streffer J. R., Tsolaki M., Schmid S., Thal D., Nicosia F., Iakovidou V., Maddalena A., Lutjohann D., Ghebremedhin E., Hegi T., Pasch T., Traxler M., Bruhl A., Benussi L., Binetti G., Braak H., Nitsch R. M., Hock C. (2003) Increased brain beta-amyloid load, phosphorylated tau, and risk of Alzheimer disease associated with an intronic CYP46 polymorphism. Arch. Neurol. 60: 29-35.

Patterson S. D., Aebersold R. (1995) Mass spectrometric approaches for the identification of gel-separated proteins. Electrophoresis 16: 1791-814.

Paul A., Cevc G., Bachhawat B. K. (1995) Transdermal immunization with large proteins by means of ultradeformable drug carriers. Eur. J. Immunol. 25: 3521-3524.

Plante-Bordeneuve V., Taussig D., Thomas F., Said G., Wood N. W., Marsden C. D., Harding A. E. (1997) Evaluation of four candidate genes encoding proteins of the dopamine pathway in familial and sporadic Parkirison's disease: evidence for association of a DRD2 allele. Neurology 48: 1589-1593.

Radebaugh T. S., Ganguli M., Khachaturian Z. D. (1999) Heterogeneity in Alzheimer's disease: implications for epidemiology. Berlin: Springer Verlag, pp.41-47.

Remington's Pharmaceutical Sciences. (1995) Mack Publishing Co., Easton, Pa., US.

Roses A. D. (1996) Apolipoprotein E alleles as risk factors in Alzheimer's disease. Review. Annu. Rev. Med. 47: 387400.

Sambrook J., Fritsch E., Maniatis T. (1989) Molecular cloning: a laboratory manual. Cold Spring Harbor Laboratory Press, Cold Spring Harbor, N.Y., USA.

Seelen M. A., Wieslander J. W., Sommarin Y., Persson A., Schlagwein N., Daha M. R., Roos A., the European Workgroup on Complement in Disease. Functional assays for the assessment of the activity of the three pathways of complement activation in a simple ELISA format. Mol. Immunol. (Special Issue: $9^{th}$ European Complement Workshop, 6-$9^{th}$ September 2003, Trieste, Italy) Vol. 40: 194.

Seelen M. A., Roos A., Wieslander J., Mollnes T. E., Sjoholm A. G., Wurzner R., Loos M., Tedesco F., Sim R. B., Garred P., Alexopoulos E., Turner M. W., Daha M. R. (2005) Functional analysis of the classical, alternative, and MBL pathways of the complement system: standardization and validation of a simple ELISA. J. Immunol. Methods 296: 187-198.

Stefanovic M., Topic E., Ivanisevic A. M., Relja M., Korsic M. (2000) Genotyping of CYP2D6 in Parkinson's disease. Clin. Chem. Lab. Med. 38: 929-934.

Steffensen R., Thiel S., Varming K., Jersild C., Jensenius J. C. (2000) Detection of structural gene mutations and promoter polymorphisms in the mannan-binding lectin (MBL) gene by polymerase chain reaction with sequence-specific primers. J. Immunol. Methods 241: 33-42.

Steffensen R., Hoffmann K., Varming K. (2003) Rapid genotyping of MBL2 gene mutations using real-time PCR with fluorescent hybridisation probes. J. Immunol. Methods. 278: 191-199.

Stuyver L., Wyseur A., van Arnhem W., Hernandez F., Maertens G. (1996) A second generation line probe assay for hepatitis C virus. J. Clin. Microbiol. 34: 2259-2266.

Stuyver L., Wyseur A., Rombout A., Louwagie J., Scarcez T., Verhofstede C., Rimland D., Schinazi R.F., Rossau R. (1997) Line probe assay (LiPA) for the rapid detection of drug-selected mutations in the HIV-1 reverse transcriptase gene. Antimicrob. Agents Chemother. 41: 284-291.

Sullivan K. E., Wooten C., Goldman D., Petri M. (1996) Mannose-binding protein genetic polymorphisms in black patients with systemic lupus erythematosus. Arthritis Rheum. 39: 2046-2051.

Super M., Thiel S., Lu J., Levinsky R. J., Turner M. W. (1989) Association of low levels of mannan-binding protein with a common defect of opsonisation. Lancet 2: 1236-1239.

Super M., Levinsky R. J., Turner M. W. (1990) The level of mannan-binding protein regulates the binding of complement-derived opsonins to mannan and zymosan at low serum concentrations. Clin. Exp. Immunol.79: 144-150.

Syvanen A. C. (2001) Accesing genetic variation: genotyping single nucleotide polymorphisms. Nat. Rev. Genet. 2: 930-942.

Tsai M. S., Tangalos E. G., Petersen R. C., Smith G. E., Schaid D. J., Kokmen E., Ivnik R. J., Thibodeau S. N. (1994) Apolipoprotein E: risk factor for Alzheimer disease. Am. J. Hum. Genet. 54: 643-649.

Turner M. W. and Hamvas R. M. J. (2000) Mannose-binding lectin: structure, function, genetics and disease associations. Rev. Immunogenetics 2: 305-322.

Turner M. W. (2003) Review. The role of mannose-binding lectin in health and disease. Mol. Immunol. 40: 423429.

Valdimarsson H., Stefansson M., Vikingsdottir T., Arason G. J., Koch C., Thiel S., Jensenius J. C. (1998) Reconstitution of opsonizing activity by infusion of mannan-binding lectin (MBL) to MBL-deficient humans. Scand. J. Immunol. 48: 116-123.

Valdimarsson H. (2003) Infusion of plasma-derived mannan-binding lectin (MBL) into MBL-deficient humans. Biochem. Soc. Trans.31 (Pt 4): 768-769.

Van Geyt C., De Gendt S., Rombaut A., Wyseur A., Maertens G., Rossau R., Stuyver L. (1998) A line probe assay for hepatitis B virus genotypes. In: R. F. Schinazi, J. P. Sommadossi, and H. Thomas (eds.). Therapies of viral hepatitis. International Medical Press, London, UK, pp. 139-145.

Wild D. (ed.) (2001) The Immunoassay Handbook $2^{nd}$ edition. Nature Pr., London, UK.

Wragg M., Hutton M., Talbot C. (1996) Genetic association between intronic polymorphism in presenilin-1 gene and late-onset Alzheimer's disease. Alzheimer's Disease Collaborative Group. Lancet 347: 509-512.

S Xiao W., Brandsma J. L. (1996) High efficiency, long-term clinical expression of cottontail rabbit papillomavirus (CRPV) DNA in rabbit skin following particle-mediated DNA transfer. Nucleic Acids Res. 24: 2620-2622.

Yan J. X., Tonella L., Sanchez J. C., Wilkins M. R., Packer N. H., Gooley A. A., Hochstrasser D. F., Williams K. L. (1997) The Dictyostelium discoideum proteome—the SWISS-2DPAGE database of the multicellular aggregate (slug). Electrophoresis 18: 491-497.

Yokota Y., Arai T., Kawasaki T. (1995) Oligomeric structures required for complement activation of serum mannan-binding proteins. J. Biochem. 117: 414419.

Zhao L. P., Li S. S., Khalid, N. (2003) A Method for the assessment of disease associations with single-nucleotide polymorphism haplotypes and environmental variables in case-control studies. American Journal of Human Genetics 72: 1231-1250.

The invention claimed is:

1. A method for determining in vitro whether a human subject is at increased risk of developing Alzheimer's disease, wherein the method comprises:
   (a) obtaining a biological sample from the subject;
   (b) detecting in the biological sample the nucleotides at positions −550, −221, +4, +154, +161, and +170 of the subject's mannan binding lectin-2 (MBL-2) gene; and
   (c) determining that the subject with a cytosine at position −550, a cytosine at position −221, a cytosine at position +4, a cytosine at position +154, a guanine at position +161, and a guanine at position +170 of the subject's MBL2 gene has increased risk of developing Alzheimer's disease relative to a subject that does not have a cytosine at position −550, a cytosine at position −221, a cytosine at position +4, a cytosine at position +154, a guanine at position +161, and a guanine at position +170.

2. The method according to claim 1, wherein the presence of each of the nucleotides at positions −550, −221, +4, +154, +161, and +170 of the subject's mannan binding lectin-2 (MBL-2) gene is identified by one of the following methods: hybridization, sequencing, Polymerase Chain Reaction (PCR), primer extension, and restriction site analysis.

3. The method according to claim 1, wherein the biological sample is a tissue sample or body fluid sample.

4. The method according to claim 3, wherein the biological sample is a brain, blood, plasma, saliva, or cerebrospinal fluid sample.

5. The method according to claim 1, wherein the method is performed in combination with the identification of one or more other risk factors for Alzheimer's disease.

6. The method according to claim 5, wherein the other risk factor is the Apolipoprotein E (ApoE) genotype, the presenilin-1 genotype, the presenilin-2 genotype, a mutation in the Amyloid Precursor Protein (APP) gene, or a Cholesterol 24-Hydroxylase (CYP46) polymorphism.

* * * * *